(12) United States Patent
Li

(10) Patent No.: US 12,376,536 B2
(45) Date of Patent: Aug. 5, 2025

(54) BREEDING METHOD AND USE OF BLUE-GRAINED TWO-LINE HYBRID WHEAT SYSTEM

(71) Applicant: Southwest University, Chongqing (CN)

(72) Inventor: Zhongan Li, Chongqing (CN)

(73) Assignee: Southwest University, Chongqing (CN)

( * ) Notice: Subject to any disclaimer, the term of this patent is extended or adjusted under 35 U.S.C. 154(b) by 245 days.

(21) Appl. No.: 17/998,341

(22) PCT Filed: Jul. 25, 2022

(86) PCT No.: PCT/CN2022/107649
§ 371 (c)(1),
(2) Date: Nov. 9, 2022

(87) PCT Pub. No.: WO2023/005883
PCT Pub. Date: Feb. 2, 2023

(65) Prior Publication Data
US 2023/0329167 A1    Oct. 19, 2023

(30) Foreign Application Priority Data
Jul. 28, 2021 (CN) .......................... 202110856412.5

(51) Int. Cl.
*A01H 1/02* (2006.01)
*A01H 1/04* (2006.01)

(52) U.S. Cl.
CPC .............. *A01H 1/021* (2021.01); *A01H 1/04* (2013.01)

(58) Field of Classification Search
CPC ..................................................... A01H 1/021
See application file for complete search history.

(56) References Cited

U.S. PATENT DOCUMENTS 12,146,148 B2 * 11/2024 Albertsen ................ A01H 5/10

FOREIGN PATENT DOCUMENTS

| CN | 1826875 A | 9/2006 |
|---|---|---|
| CN | 100420368 C | 9/2008 |
| CN | 103270935 A | 9/2013 |
| CN | 104719129 A | 6/2015 |
| CN | 108342502 A | 7/2018 |
| CN | 108496791 A | 9/2018 |
| CN | 111511199 A | 8/2020 |
| CN | 113557957 A | 10/2021 |
| WO | 93/13649 A1 | 7/1993 |
| WO | 98/51142 A1 | 11/1998 |
| WO | 2002/052924 A2 | 7/2002 |

OTHER PUBLICATIONS

Dvorak et al Theoretical and Applied Genetics 131:2451-2462 (Year: 2018).*
Buresova et al. "Variation in genome composition of blue-aleurone wheat" Theor Appl Genet (2015) 128:273-282, Published online: Nov. 16, 2014.
Chinese First Office Action for Chinese Application No. 202110856412.5, dated Mar. 8, 2022, 9 pages with English translation.
Chinese Second Office Action for Chinese Application No. 202110856412.5, dated Oct. 18, 2022, 9 pages with English translation.
Darvey "Selection and Identification of Wheat Alien" Journal of Xi'an United University, vol. 4, No. 2, Apr. 2001, 6 pages.
International Search Report for International Application No. PCT/CN2022/107649, mailed Oct. 8, 2022, 7 pages with English translation.
Xing et al. "Study on Blue Seed Dual-purpose Wheat" Journal of Shanxi Agricultural Sciences( 2009) 37(3) pp. 33-35 (English Abstract).
Zheng et al. "Utilization of blue-grained character in wheat breeding derived from Thinopyrum poticum" J. Genet. Genomics 36 (2009) 575-580, accepted Apr. 29, 2009.

* cited by examiner

*Primary Examiner* — Brent T Page
(74) *Attorney, Agent, or Firm* — TraskBritt

(57) ABSTRACT

The present disclosure discloses a breeding method and use of a blue-grained two-line hybrid wheat system. The present disclosure creates alien translocated chromosomes (T4AgL (Ba-containing fragment)-4BL (fragment near centromere) .4thS and T4AgL (Ba-containing fragment)-4BL (fragment near centromere).4thS (Rf-containing fragment)) and alien translocated telosomes (T4AgL (Ba-containing fragment)-4thS (Rf-containing fragment), T4thS (Rf-containing fragment)-4AgL (Ba-containing fragment). and T4thS (Rf-containing fragment)-4AgL (Ba-containing fragment)-4BL (fragment near centromere).) of a blue-grained gene Ba and an alien restoring gene Rf, which exhibit xenia and dose-response and can lead to complete recovery of a recessive genetic male sterility (GMS) gene ms1. In this way, the present disclosure completes the improvement of a blue-grained two-line hybrid wheat system.

1 Claim, 6 Drawing Sheets

BREEDING METHOD AND USE OF BLUE-GRAINED TWO-LINE HYBRID WHEAT SYSTEM

CROSS-REFERENCE TO RELATED APPLICATIONS

This application is a national phase entry under 35 U.S.C. § 371 of International Patent Application PCT/CN2022/107649, filed Jul. 25, 2022, designating the United States of America and titled BREEDING METHOD AND USE OF BLUE-GRAINED TWO-LINE HYBRID WHEAT SYSTEM, which claims the benefit under Article 8 of the Patent Cooperation Treaty to Chinese Patent Application Serial No. 2021108564125, filed Jul. 28, 2021.

TECHNICAL FIELD

The present disclosure belongs to the field of crop genetics and breeding, and relates to a breeding method and use of a blue-grained two-line hybrid wheat system.

BACKGROUND

Wheat is a food crop with the largest consumption worldwide. With the reduction of arable land and the increase of population, it is imperative to increase wheat yield per unit. The utilization of heterosis is an important way to increase crop yield per unit. Hybridization has long been achieved in crops such as rice, corn, and sorghum, and resulting hybrid crops have been widely used in production, which greatly increases the yield. The utilization of wheat heterosis has always been a challenge in the world, and no breakthrough has been made in production. This is mainly because wheat is a polyploid requiring a large seeding amount, and its heterosis is not as strong as heterosis of a crop such as rice, corn, and sorghum. Therefore, a feasible hybrid wheat system is the key to produce high-yield and low-cost hybrid seeds.

Since the Japanese scientist Kihara first discovered a cytoplasmic male sterile (CMS) wheat line in 1951, scientists and some well-known seed companies or biotechnological breeding companies have successively established and tried a variety of hybrid wheat systems, including a CMS system, a chemical hybridization agent (CHA) system, a photo-thermo-sensitive cytoplasmic male sterility (PCMS) system, and a genetic male sterility (GMS) system. However, due to some defects or deficiencies of these systems, it is difficult to achieve large-scale production.

Driscoll has established an XYZ system and an improved XYZ system successively, both of which are GMS systems and utilize a dominant male fertility gene and a panicle/stalk villus dominant marker gene carried by the chromosome 5R of rye. Because the panicle/stalk villus dominant marker can only be identified after wheat heading, it is obviously not practical for wheat cultivated at a high density, but it has important guiding significance for the establishment and application of GMS systems. Huang et al. (1991) and Zhou et al. (1998) successively established blue-grained hybrid wheat systems marked by blue grains similar to the XYZ system, where an effective marker is provided, and a sterile line and a maintainer line are distinguished according to grain colors. However, due to the unsatisfactory self-seeding of a blue-grained dual-purpose line, it is difficult to breed a strong heterosis hybrid variety for production. Although blue-grained plants have an improved self-seeding set (30% to 80%), there are adverse effects such as albino seedlings and yellow seedlings (Liu et al., 2004). Hybrid wheat systems marked by blue grains can also be seen in the Australian patent "Genetically modified wheat plants and progeny and method for production of hybrid wheat (PCT/AU93/00017(WO93/13649))" and the Israeli patent "Methods for production of hybrid wheat (PCT/IL98/00220 (WO98/51142))," and there is no report on the research and application of these systems. With the method for breeding two-line hybrid wheat marked by blue grains (CN200610042629.8), a batch of sterile lines and 3 provincially approved hybrids have been cultivated, a batch of crossing combinations are being tested, and more hybrid varieties will be approved and promoted in succession. Both seed sorting and seed production meet the requirements of hybrid wheat, but the additional translocated chromosome still needs to be improved in its stability. A frequency of breakage of this additional chromosome at a centromere is high (0.5% to 10%), and it is difficult to breed a dual-purpose line with a low breakage frequency.

Most of male sterility genes in wheat are produced through natural mutation or artificial induction. Many GMS materials have been found and induced, and sterility genes in these materials include ms1 (recessive), Ms2 (dominant), Ms3 (dominant), Ms4 (dominant), and ms5 (recessive), which are located on chromosome arms 4BS, 4DS, 5AS, 4DS, and 3AL, respectively. There are many mutants at the locus ms1, including a Pugsley's mutant (with an allele ms1a), a Probus mutant (with an allele ms1b), a Cornerstone mutant (with an allele ms1c), an FS2 mutant (with an allele ms1d), an FS3 mutant (with an allele ms1e), an FS24 mutant (with an allele ms1f), an LZ mutant (with an allele ms1g), mutants of Ningchun 4 series (with allele series ms1h-p), and the like.

Wazuddin and Driscoll (1986) introduced chromosome 4 of each of the diploid wheat varieties (Einkorn) *Triticum thaoudar* (=*T. boeoticum*), *T. urartu*, and *T. monococcum* into a hexaploid common wheat variety (*T. aestivum*), and it was found that this chromosome could not pair with any chromosome of the common wheat, indicating that the chromosome 4 of Einkorn does not exist in the common wheat. A restoring gene (Rf) carried by the chromosome can completely restore the sterility gene ms1. Morrison et al. (2004) described the origins and differences of blue-grained genes (Ba), where blue-grained genes that exhibit xenia and dose-response are derived from chromosomes 4Ag of *Agropyron elongatum* (Host) Beauv. and *A. intermedium* (Host) Beauv. (*A. tricophorum K. Richter*) (2n=10×=70), and blue-grained genes that do not exhibit xenia are derived from chromosome 4 of *T. boeoticum* (=*T. thaoudar*). There is a blue-grained gene that does not exhibit xenia on a long arm of chromosome 4 of *T. boeoticum*, which indirectly proves that this chromosome does not belong to the common wheat. Only a blue-grained gene exhibiting xenia and dose-response can be used as a marker to determine whether a wheat grain includes a blue-grained gene and how many copies of the blue-grained gene are included in the wheat grain (the endosperm and aleurone layer are triploids, with 1 copy from the father and 2 copies from the mother). When only a male gamete (pollen) includes a blue-grained gene, generated grains are light blue and include 1 Ba copy (grains obtained from selfing include non-blue grains, light-blue grains, medium-blue grains, and dark-blue grains); when only a female gamete includes a blue-grained gene, generated grains are medium-blue and include 2 Ba copies (grains obtained from selfing include non-blue grains, light-blue grains, medium-blue grains, and dark-blue grains); and when both male and female gametes include a blue-grained gene, generated grains are dark blue and include 3 Ba copies (grains obtained from selfing are all blue). The research of the present disclosure shows that the chromosome 4 of *T. thaoudar* (=*T. boeoticum*) named as 4th is superior to chromosomes 4 of *T. urartu* and *T. monococcum* in terms of the influence on agronomic traits of wheat.

There are many methods for inducing chromosomal translocation, mainly including the following five methods: 1) spontaneous translocation resulting from misdivision and un-stability of alien monosomic chromosomes; 2) radiation treatment; 3) chemical mutagenesis by dimethylsulfoxide (DMSO), ethyl methanesulfonate (EMS), and the like; 4) induction of some homologous chromosome pairing to produce translocation; and 5) tissue culture. It has been proved by practices that a frequency of chromosomal translocation is generally 1% or lower. Hu Yingkao describes 37 wheat-alien translocation lines, among which 15 are obtained through radiation, 11 are obtained through partial homologous recombination, 6 are obtained through spontaneous translocation, and 3 are obtained through tissue culture. Friebe et al. set forth 57 spontaneous or induced wheat-alien translocation chromosomes, among which 10 undergo translocation at a centromere, 45 undergo translocation at an end, and 2 undergo translocation at a middle. This provides a basis for the creation of an alien translocated chromosome carrying a blue-grained gene Ba, which exhibits xenia and dose-response and can lead to complete recovery of the sterility gene ms1.

BRIEF SUMMARY

The present disclosure is conducted on the basis of the "method for breeding two-line hybrid wheat marked by blue grains (CN200610042629.8)." In CN200610042629.8, a breeding method is established, in which an original dual-purpose line of the karyotype-sterile hybrid wheat system is separated with blue grains as a marker trait and then a new dual-purpose line is established. The breeding method specifically includes the following steps:

1) Establishment of an Original Light-Blue-Grained Dual-Purpose Line in this System a. Creation of an Exogenous Additional Translocated Chromosome T4thS.4AgL (Referred to as 4thS.4AgL in CN200610042629.8)

In order to ensure the authenticity and reliability of base materials, the translocated chromosome T4BS.4AgL translocated chromosome and the wheat 4B substitution line 4th derived from chromosome 4 of *T. thaoudar* are identified through chromosome banding and alcohol dehydrogenase electrophoresis analysis, and a sterility gene ms1b and a dwarfing gene Rht3 located on a short arm of the wheat chromosome 4B are linked together through genetic recombination; then the sterility gene ms1b and the dwarfing gene Rht3 are simultaneously recombined into the translocated chromosome T4BS.4AgL to obtain a blue-grained dwarf sterile plant;

the blue-grained dwarf sterile plant is crossed with the wheat 4B substitution line 4$^{th}$" of the chromosome 4th to obtain a diploid wheat plant carrying 4th and a chromosome T4BS.4AgL with genes ms1b and Rht3 ($F_1$), enough $F_2$ white or red, light-blue, and dark-blue seeds are obtained through selfing, and only the $F_2$ dark-blue seeds are sown; all tall fertile plants in the $F_2$ population are numbered and crossed as a male parent with a sterile plant in a derived line carrying a sterility gene ms1b of a "Probus" mutant, and only hybrid ears with light-blue seeds are harvested; hybrid $F_1$ light-blue seeds are sown, seedlings are bagged after heading, and a hybrid combination whose all individual plants are fertile is screened out; and robust individual plants are selected, light-blue, white, or red seeds are sorted and sown to observe the fertility, and a light-blue-grained line in which all plants grown from white or red seeds are sterile and all plants grown from corresponding light-blue seeds are fertile is screened out, where the light-blue-grained line includes a desired translocated chromosome T4thS.4AgL that integrates an exogenous restoring gene and a blue-grain gene;

or, the diploid wheat plant carrying the 4th and the chromosome T4BS.4AgL with genes ms1b and Rht3 is directly crossed as a male parent with a sterile plant without the dwarfing gene Rht3 in the derived line carrying the sterility gene ms1b of the "Probus" mutant, enough $F_1$ blue-grained seeds are harvested and sown to cultivate plants, tall fertile plants are numbered and then each crossed with a sterile plant without the dwarfing gene Rht3 in the derived line carrying the sterility gene ms1b of the "Probus" mutant; and blue seeds are also selected and sown to observe the fertility, and a combination whose all plants are fertile is screened out to obtain a line carrying a translocated chromosome T4thS.4AgL.

b. Screening and Identification of the Original Dual-Purpose Line

The above line carrying the translocated chromosome T4thS.4AgL is selfed or further crossed with a sterile plant without the dwarfing gene Rht3 in the derived line carrying the sterility gene ms1b of the "Probus" mutant and then selfed, an individual plant in which a ratio of blue grains to white or red grains is 1:2 is screened out from a progeny population, a dual-purpose line is preliminarily screened out, and then the chromosome pairing in a meiotic metaphase of pollen mother cells is confirmed through microscopic examination to obtain the original dual-purpose line 21II+ $I_{4ths.4AgL}$ of the hybrid wheat system.

2) Breeding Method of the New Dual-Purpose Line

Method 1: The original dual-purpose line is used to prepare hybrid combinations with excellent lines; in the $F_1$ generation, only blue seeds are selected and sown; according to the performance of each combination, excellent combinations are selected, light-blue seeds are sorted from $F_2$ seeds of the selected combinations and sown, and excellent individual plants are screened out; white or red seeds and light-blue seeds in each line of the $F_3$ generation are sown separately to obtain 50 plants for each color; a corresponding light-blue-grained line with prominent agronomic traits in which 25% or 100% of a white-grained or red-grained population are sterile plants is screened out, and a dual-purpose line is obtained after the agronomic traits are stabilized; the above operations are repeated until the line is stable and the separated white-grained or red-grained plants are all sterile; and a yield of the dual-purpose line is tested and the separated white or red seeds are subjected to quality analysis and disease resistance identification to obtain a new dual-purpose line with high yield, high quality, and multi-resistance.

Method 2: An excellent sterile plant separated from a $F_2$ population of the crossing between a sterile line and a conventional excellent line is selected and crossed as a female parent with the original dual-purpose line; and similar to the method 1, excellent combinations and excellent individual plants are screened out in $F_1$ and $F_2$ generations, and excellent lines are screened out in $F_3$ or higher generations, but only light-blue seeds are sown in $F_3$ or higher generations until a sterile line is required. This method does not require emasculation during crossing, and is suitable for the utilization of excellent sterile plants separated from a $F_2$ population of a strong dominant combination.

The present disclosure is intended to provide a breeding method and use of a blue-grained two-line hybrid wheat system.

1. The present disclosure provides a breeding method of a blue-grained two-line hybrid wheat system, including the following steps:
   (1) crossing white-grained sterile plants of a dual-purpose line 06L6109-3 with wheat plants carrying a translocated chromosome T4AgL(Ba)-4BL.4BS, and screening out dwarf and male-sterile plants grown from blue seeds, which are plants carrying the translocated chromosome T4AgL(Ba)-4BL.4BS (Rht3-ms1b) and are called a T4AgL(Ba)-4BL.4BS (Rht3-ms1b) translocation plant line,
   where the wheat plant carrying the translocated chromosome T4AgL(Ba)-4BL.4BS grows from a blue seed and is tall and male-fertile; the white-grained sterile plant is a dwarf and male-sterile plant grown from a white seed obtained from selfing of the dual-purpose line 06L6109-3; and the dual-purpose line 06L6109-3 is an Rht3-ms1b-containing blue-grained dual-purpose line bred from a cross between Rht3-ms1b-containing semi-dwarf and male-sterile wheat plants grown from white seeds and wheat plants of an addition line carrying a translocated chromosome T4hS.4AgL;
   (2) crossing the T4AgL(Ba)-4BL.4BS (Rht3-ms1b) translocation plant line with a wheat 4B substitution line carrying 4th to obtain double monosomic seeds carrying the 4th and the translocated chromosome T4AgL (Ba)-4BL.4BS (Rht3-ms1b);
   (3) sowing the double monosomic seeds obtained in step (2) to cultivate plants, selfing the plants, selecting and sowing dark-blue seeds, and screening out tall and male-fertile plants;
   (4) crossing the plants screened out in step (3) with white-grained sterile plants of a dual-purpose line 14L6386 individually, and screening out crosses with blue seeds,
   where the white-grained sterile plants of the dual-purpose line 14L6386 are male-sterile plants grown from white seeds obtained from selfing of the dual-purpose line 14L6386; the dual-purpose line 14L6386 is a blue-grained dual-purpose line bred by a cross between a dual-purpose line 09L6034 and a waxy wheat line; the dual-purpose line 09L6034 is a blue-grained dual-purpose line bred by backcrossing a dual-purpose line T0065-10B-2LB-4 with a wheat recurrent parent Zhou 88114 (named Zhoumai 11); and the dual-purpose line T0065-10B-2LB-4 is a wheat addition line carrying the translocated chromosome T4hS.4AgL;
   (5) according to a screening result in step (4), sowing blue seeds of a cross to cultivate plants, where if plants grown from all blue seeds of the cross are male-fertile plants, the plants grown from the seeds constitute a potential translocation line;
   (6) selfing the potential translocation line obtained in step (5), harvesting seeds, classifying blue seeds and white seeds into group separately; sowing the blue seeds and the white seeds separately to cultivate plants; and if all individual plants grown from the blue seeds are male-fertile plants and all individual plants grown from the white seeds are male-sterile plants, subjecting the male-fertile plants grown from the blue seeds to fluorescence in situ hybridization (FISH) identification, and screening out individual plants carrying a translocated chromosome T4AgL fragment (Ba)-4BL.4thS (Rf), which constitute a T4AgL fragment (Ba)-4BL.4thS (Rf) translocation line; and
   (7) from selfed progeny of the translocation line obtained in step (6), screening out a plant line in which a number of white seeds and a number of blue seeds are in a ratio of 2:1, which is an addition line carrying the translocated chromosome T4AgL fragment (Ba)-4BL.4thS (Rf) and is also known as a dual-purpose line.

The dual-purpose line may have a karyotype of 21 II $(msms)+I_{T4AgL\ fragment\ (Ba)-4BL.4thS\ (Rf)}$.

2. The present disclosure provides a breeding method of a blue-grained two-line hybrid wheat system, including the following steps:
   (1) selfing a dual-purpose line 15L4167, and screening out male-sterile plants grown from blue seeds obtained from the selfing; crossing the male-sterile plants with dark-blue-grained fertile plants, and screening out and selfing a male-fertile plant grown from a dark-blue seed obtained from the crossing; and screening out male-sterile plants from plants grown from selfed seeds, and further conducting microscopic screening to obtain an addition line carrying a translocated telosome T4AgL fragment (Ba)-4BL., where the dark-blue-grained fertile plants are male-fertile planta grown from dark-blue seeds obtained from selfing of the dual-purpose line 15L4167, and seeds produced after selfing of the dark-blue-grained fertile plants are all blue seeds;
   (2) selfing the dual-purpose line 15L4167, selecting male-fertile plants grown from white seeds obtained from the selfing, and further conducting microscopic screening to obtain an addition line carrying a telosome 4thS (Rf).;
   (3) crossing the addition line carrying the telosome 4thS (Rf) as a male parent with the addition line carrying the translocated telosome T4AgL fragment (Ba)-4BL as a female parent to obtain double-mono-telosomic seeds carrying the translocated telosome T4AgL fragment (Ba)-4BL and the telosome 4thS (Rf).;
   (4) cultivating male and female parent plants with the seeds obtained in step (3) as a male parent and white seeds as a female parent, crossing the male and female parent plants, and screening out blue seeds from seeds obtained from the female parent plants, where the white seeds are obtained from selfing of the dual-purpose line 15L4167;
   (5) sowing the blue seeds obtained in step (4) to cultivate plants, eliminating male-sterile plants, harvesting male-fertile plants, conducting seed selection, and sowing selected seeds to cultivate plants each with both blue seeds and white seeds;
   (6) sorting white seeds and blue seeds of each of the plants obtained in step (5); and
   (7) sowing the white seeds and the blue seeds obtained in step (6) to cultivate plants; and if all plants grown from blue seeds of an individual plant are male-fertile plants and all plants grown from white seeds of the individual plant are male-sterile plants, subjecting light-blue seeds of the individual plant to microscopic examination to obtain a translocation line carrying a translocated chromosome T4AgL fragment (Ba)-4BL.4thS fragment (Rf), which is also known as a dual-purpose line,
   where the dual-purpose line 15L4167 is the addition line carrying the translocated chromosome T4AgL fragment (Ba)-4BL.4thS (Rf) described above.

The dual-purpose line may have a karyotype of 21 II (msms)+I$_{T4AgL\ fragment\ (Ba)\text{-}4BL.4thS\ fragment\ (Rf)}$.

3. The present disclosure provides a breeding method of a blue-grained two-line hybrid wheat system, including the following steps:
   (1) selfing a dual-purpose line 16L6386, harvesting and sowing blue seeds to cultivate plants, selecting male-sterile plants, and screening out male-sterile plants carrying a telosome 4AgL(Ba). through microscopic examination; and selfing the dual-purpose line 16L6386, harvesting and sowing dark-blue seeds to cultivate plants, which are male-fertile plants;
   (2) crossing the male-sterile plants screened out in step (1) with the male-fertile plants screened out in step (1), screening out and sowing dark-blue seeds to cultivate plants, and screening out male-sterile plants from selfed progeny of the plants;
   (3) selfing the dual-purpose line 16L6386, harvesting and sowing white seeds to cultivate plants, selecting male-fertile plants, and screening out a male-fertile plant carrying a telosome 4thS(Rf). through microscopic examination;
   (4) crossing the male-sterile plants screened out in step (2) with the male-fertile plants screened out in step (3), harvesting and sowing seeds to cultivate plants, selfing the plants, selecting dark-blue seeds, and screening out and multiplying a double-ditelosomic seed carrying both a pair of a telosome 4AgL(Ba). and a pair of a telosome 4thS(Rf). through microscopic examination;
   (5) subjecting the double-ditelosomic seeds multiplied in step (4) to a mutagenesis treatment, and sowing the double-ditelosomic seeds to cultivate plants;
   (6) crossing the plants grown from the double-ditelosomic seeds obtained in step (4) as a male parent with white-grained sterile plants as a female parent, harvesting seeds on the female parent plants, selecting blue seeds, subjecting the blue seeds to a mutagenesis treatment, and sowing the blue seeds to cultivate plants, where the white-grained sterile plants are male-sterile plants grown from white seeds obtained from selfing of the dual-purpose line 16L6386;
   (7) crossing the plants obtained in step (5) or (6) as a male parent with white-grained sterile plants as a female parent, harvesting seeds on the female parent plant, and screening out blue seeds, where the white-grained sterile plants are male-sterile plants grown from white seeds obtained from selfing of the dual-purpose line 16L6386;
   (8) sowing the blue seeds obtained in step (7) to cultivate plants, eliminating male-sterile plants, selfing selected plants, harvesting seeds, and sowing selected seeds to cultivate plants each with both blue seeds and white seeds;
   (9) sorting white seeds and blue seeds obtained from selfing of each of the plants screened out in step (8); and
   (10) sowing the white seeds and the blue seeds obtained in step (9) to cultivate plants; and if all plants grown from blue seeds of an individual plant are male-fertile plants and all plants grown from white seeds of the individual plant are male-sterile plants, subjecting blue seeds of the individual plants to microscopic examination to obtain a plant line carrying a translocated telosome T4AgL fragment (Ba)-4thS fragment (Rf)., which is a dual-purpose line with light-blue/medium-blue seeds, where the dual-purpose line 16L6386 is a wheat addition line carrying a translocated chromosome T4thS.4AgL.

The dual-purpose line may have a karyotype of 21 II (msms)+I$_{T4AgL\ fragment\ (Ba)\text{-}4thS\ fragment\ (Rf)}$.

4. The present disclosure provides a breeding method of a blue-grained two-line hybrid wheat system, including the following steps:
   (1) selfing a dual-purpose line 16L6386, harvesting and sowing blue seeds to cultivate plants, selecting male-sterile plants, and screening out male-sterile plants carrying a telosome 4AgL(Ba). through microscopic examination; and selfing the dual-purpose line 16L6386, harvesting and sowing a dark-blue seed to cultivate a plant, which is a male-fertile plant;
   (2) crossing the male-sterile plants screened out in step (1) with the male-fertile plants screened out in step (1), screening out and sowing dark-blue seeds to cultivate plants, and screening out male-sterile plants from selfed progeny of the plants;
   (3) selfing the dual-purpose line 16L6386, harvesting and sowing white seeds to cultivate plants, selecting male-fertile plants, and screening out a male-fertile plant carrying a telosome 4thS(Rf). through microscopic examination;
   (4) crossing the male-sterile plants screened out in step (2) with the male-fertile plants screened out in step (3), harvesting and sowing seeds to cultivate plants, selfing the plants, selecting dark-blue seeds, and screening out a double-ditelosomic seed carrying both a pair of a telosome 4AgL(Ba). and a pair of a telosome 4thS(Rf). through microscopic examination;
   (5) subjecting the double-ditelosomic seeds screened out in step (4) to a mutagenesis treatment, and sowing the double-ditelosomic seeds to cultivate plants;
   (6) crossing the plants grown from the double-ditelosomic seeds obtained in step (4) as a male parent with white-grained sterile plants as a female parent, harvesting seeds on the female parent plants, selecting blue seeds, subjecting the blue seeds to a mutagenesis treatment, and sowing the blue seeds to cultivate plants, where the white-grained sterile plants are male-sterile plants grown from white seeds obtained from selfing of the dual-purpose line 16L6386;
   (7) crossing the plants obtained in step (5) or (6) as a male parent with white-grained sterile plants as a female parent, harvesting seeds on the female parent plants, and screening out blue seeds, where the white-grained sterile plants are male-sterile plants grown from white seeds obtained from selfing of the dual-purpose line 16L6386;
   (8) sowing the blue seeds obtained in step (7) to cultivate plants, eliminating male-sterile plants, selfing a selected plant, harvesting seeds, and sowing selected seeds to cultivate plants each with both blue seeds and white seeds;
   (9) sorting white seeds and blue seeds obtained from selfing of each of the plants screened out in step (8); and
   (10) sowing the white seeds and the blue seeds obtained in step (9) to cultivate plants; and if all plants grown from blue seeds of an individual plant are male-fertile plants and all plants grown from white seeds of the individual plant are male-sterile plants, subjecting blue seeds of the individual plant to microscopic examination to obtain a plant line carrying a translocated telosome T4thS fragment (Rf)-4AgL fragment (Ba)., which is a dual-purpose line with light-blue/medium-blue seeds, where the dual-purpose line 16L6386 is a wheat addition line carrying a translocated chromosome T4thS.4AgL.

The dual-purpose line may have a karyotype of 21 II (msms)+$I_{T4thS\ fragment\ (Rf)\text{-}4thS\ fragment\ (Ba)}$.

5. The present disclosure provides a breeding method of a blue-grained two-line hybrid wheat system, including the following steps:

(1) propagating the double-ditelosomic seeds carrying both a pair of a translocated telosome T4AgL fragment (Ba)-4BL. and a pair of a telosome 4thS (Rf). obtained in step (3) of 2;

(2) subjecting the double-ditelosomic seed obtained in step (1) to a mutagenesis treatment, and sowing the double-ditelosomic seeds to cultivate plants;

(3) crossing the plants grown from the double-ditelosomic seeds obtained in step (1) as a male parent with white-grained sterile plants obtained from selfing of a dual-purpose line 15L4167 as a female parent, harvesting seeds on the female parent plants, selecting blue seeds, subjecting the blue seeds to a mutagenesis treatment, and sowing the blue seeds to cultivate plants, where the white-grained sterile plants are male-sterile plants grown from white seeds obtained from selfing of a dual-purpose line 15L4167, and the dual-purpose line 15L4167 is the addition line carrying the translocated chromosome T4AgL fragment (Ba)-4BL.4thS (Rf) described above;

(4) crossing the plants obtained in step (2) or (3) as a male parent with white-grained sterile plants as a female parent, harvesting seeds on the female parent plants, and screening out blue seeds, where the white-grained sterile plants are male-sterile plants grown from white seeds obtained from selfing of a dual-purpose line 15L4167, and the dual-purpose line 15L4167 is the addition line carrying the translocated chromosome T4AgL fragment (Ba)-4BL.4thS (Rf) described above;

(5) sowing the blue seeds obtained in step (4) to cultivate plants, eliminating male-sterile plants, selfing selected plants, harvesting seeds, and sowing selected seeds to cultivate plants each with both blue seeds and white seeds;

(6) sorting white seeds and blue seeds obtained from selfing of each of the plants screened out in step (5); and (7) sowing the white seeds and the blue seeds obtained in step (6) to cultivate plants; and if all plants grown from blue seeds of an individual plant are male-fertile plants and all plants grown from white seeds of the individual plant are male-sterile plants, subjecting blue seeds of the individual plant to microscopic examination to obtain a plant line carrying a translocated telosome T4thS fragment (Rf)-4AgL fragment (Ba)-4BL., which is a dual-purpose line with light-blue/medium-blue seeds.

The dual-purpose line may have a karyotype of 21 II (msms)+$I_{T4thS\ fragment\ (Rf)\text{-}4AgL\ fragment\ (Ba)\text{-}4BL}$.

The method may specifically include the following steps:

(1) crossing white-grained sterile plants of a dual-purpose line 06L6109-3 with wheat plants carrying a translocated chromosome T4AgL(Ba)-4BL.4BS, and screening out dwarf and male-sterile plant grown from blue seeds, which are plants carrying the translocated chromosome T4AgL(Ba)-4BL.4BS (Rht3-ms1b) and is called a T4AgL(Ba)-4BL.4BS (Rht3-ms1b) translocation plant line, where the wheat plants carrying the translocated chromosome T4AgL(Ba)-4BL.4BS grows from blue seeds and are tall and male-fertile; the translocated chromosome T4AgL(Ba)-4BL.4BS is obtained by recombining 4AgL(Ba) into 4B; the white-grained sterile plants of the dual-purpose line 06L6109-3 are dwarf and male-sterile plants grown from white seeds obtained from selfing of the dual-purpose line 06L6109-3; and the dual-purpose line 06L6109-3 is an Rht3-ms1b-containing blue-grained dual-purpose line obtained by a cross between Rht3-ms1b-containing semi-dwarf and male-sterile wheat plants grown from white seeds and wheat plants of an addition line carrying a translocated chromosome T4thS.4AgL;

(2) crossing the T4AgL(Ba)-4BL.4BS (Rht3-ms1b) translocation plant line (homozygote) with a wheat 4B substitution line carrying 4th to obtain a double monosomic seeds carrying the 4th and the translocated chromosome T4AgL(Ba)-4BL.4BS (Rht3-ms1b);

(3) sowing the double monosomic seeds obtained in step (2) to cultivate plants, selfing the plants, selecting and sowing dark-blue seeds, and screening out tall and male-fertile plants;

(4) crossing the plant screened out in step (3) with white-grained sterile plants of a dual-purpose line 14L6386 individually, and screening out crosses with blue seeds;

(5) according to a screening result in step (4), sowing blue seeds of a cross to cultivate plants, where if plants grown from all blue seeds of the cross are male-fertile plants, the plants grown from the seeds constitute a potential translocation line;

(6) selfing the potential translocation line obtained in step (5), harvesting seeds, classifying blue seeds and white seeds into group separately; sowing the blue seeds and the white seeds separately to cultivate plants; and if all individual plants grown from the blue seeds are male-fertile plants and all individual plants grown from the white seeds are male-sterile plants, subjecting the male-fertile plants grown from the blue seeds to FISH identification, and screening out individual plants carrying a translocated chromosome T4AgL fragment (Ba)-4BL.4thS (Rf), which constitute a T4AgL fragment (Ba)-4BL.4thS (Rf) translocation line; and (7) from selfed progeny of the translocation line obtained in step (6), screening out a plant line in which a number of white seeds and a number of blue seeds are in a ratio of 2:1, which is an addition line carrying the translocated chromosome T4AgL fragment (Ba)-4BL.4thS (Rf) (a dual-purpose line).

The dual-purpose line may have a karyotype of 21 II (msms)+$I_{T4AgL\ fragment\ (Ba)\text{-}4BL.4thS\ (Rf)}$.

The method may specifically include the following steps:

(1) selfing a dual-purpose line 15L4167, and screening out male-sterile plants grown from blue seeds obtained from the selfing line, which are plants carrying a translocated telosome T4AgL fragment (Ba)-4BL.; crossing the male-sterile plants with a dark-blue-grained fertile plants (the dark-blue-grained fertile plants are male-fertile plants grown from dark-blue seeds obtained from selfing of the dual-purpose line 15L4167, and seeds produced after selfing of the dark-blue-grained fertile plants are all blue seeds), and screening out and selfing male-fertile plants grown from dark-blue seeds obtained from the crossing; and screening out male-sterile plants from plants grown from selfed seeds, and further conducting microscopic screening to obtain an addition line carrying a translocated telosome T4AgL fragment (Ba)-4BL.;

(2) selfing the dual-purpose line 15L4167, selecting male-fertile plants grown from white seeds obtained from the selfing (which are plants carrying a telosome 4thS (Rf).), and further conducting microscopic screening to obtain an addition line carrying a telosome 4thS (Rf).;

(3) crossing the addition line carrying the telosome 4thS (Rf). as a male parent with the addition line carrying the translocated telosome T4AgL fragment (Ba)-4BL. as a female parent to obtain a ditelosomic seed carrying the translocated telosome T4AgL fragment (Ba)-4BL. and the telosome 4thS (Rf).;

(4) cultivating male and female parent plants with the seeds obtained in step (3) as a male parent and white seeds (the white seeds are obtained from selfing of the dual-purpose line 15L4167) as a female parent, crossing the male and female parent plants, and screening out blue seeds from seeds obtained from the female parent plants;

(5) sowing the blue seeds obtained in step (4) to cultivate plants, eliminating male-sterile plants, harvesting male-fertile plants, subjecting the harvested male-fertile plants to seed selection, and sowing selected seeds to cultivate plants each with both blue seeds and white seeds;

(6) sorting white seeds and blue seeds of each of the plants obtained in step (5); and (7) sowing the white seeds and the blue seeds obtained in step (6) to cultivate plants; and if all plants grown from blue seeds of an individual plant are male-fertile plants and all plants grown from white seeds of the individual plant are male-sterile plants, subjecting light-blue seeds of the individual plant to microscopic examination to obtain a translocation line carrying a translocated chromosome T4AgL fragment (Ba)-4BL.4thS fragment (Rf), which is a dual-purpose line with light-blue/medium-blue seeds.

The dual-purpose line may have a karyotype of 21 II $(msms)+I_{T4AgL\ fragment\ (Ba)-4BL.4thS\ fragment\ (RF)}.$ The method may specifically include the following steps:

(1) selfing a dual-purpose line 16L6386, harvesting and sowing blue seeds to cultivate plants, selecting male-sterile plants, and screening out male-sterile plants carrying a telosome 4AgL(Ba). through microscopic examination; and selfing the dual-purpose line 16L6386, harvesting and sowing dark-blue seeds to cultivate plants, which are male-fertile plants;

(2) crossing the male-sterile plants screened out in step (1) with the male-fertile plants screened out in step (1), screening out and sowing dark-blue seeds to cultivate plants, and screening out male-sterile plants from selfed progeny of the plants;

(3) selfing the dual-purpose line 16L6386, harvesting and sowing white seeds to cultivate plants, selecting male-fertile plants, and screening out a male-fertile plant carrying a telosome 4thS(Rf). through microscopic examination;

(4) crossing the male-sterile plants screened out in step (2) with the male-fertile plants screened out in step (3), harvesting and sowing blue seeds to cultivate plants, selfing the plants, selecting dark-blue seeds, and screening out a double-ditelosomic seeds carrying both a pair a telosome 4AgL(Ba). and a pair of a telosome 4thS(Rf). through microscopic examination;

(5) subjecting the double-ditelosomic seed screened out in step (4) to a mutagenesis treatment, and sowing the double-ditelosomic seeds to cultivate plants;

(6) crossing the plants grown from the double-ditelosomic seeds obtained in step (4) as a male parent with a white-grained sterile plants (the white-grained sterile plants are male-sterile plants grown from white seeds obtained from selfing of the dual-purpose line 16L6386) as a female parent, harvesting seeds on the female parent plants, selecting blue seeds, subjecting the blue seeds to a mutagenesis treatment, and sowing the blue seeds to cultivate plants;

(7) crossing the plants obtained in step (5) or (6) as a male parent with white-grained sterile plants (the white-grained sterile plants are male-sterile plants grown from white seeds obtained from selfing of the dual-purpose line 16L6386) as a female parent, harvesting seeds on the female parent plant, and screening out blue seeds;

(8) sowing the blue seeds obtained in step (7) to cultivate plants, eliminating male-sterile plants, selfing selected plants, harvesting seeds, and sowing selected seeds to cultivate plants each with both blue seeds and white seeds;

(9) sorting white seeds and blue seeds obtained from selfing of each of the plants screened out in step (8); and

(10) sowing the white seeds and the blue seeds obtained in step (9) to cultivate plants; and if all plants grown from blue seeds of an individual plant are male-fertile plants and all plants grown from white seeds of the individual plant are male-sterile plants (this individual plant is a potential telosome-containing plant), subjecting blue seeds of the individual plant to microscopic examination to obtain a plant line carrying a translocated telosome T4AgL fragment (Ba)-4thS fragment (Rf)., which is a translocation line carrying a translocated telosome T4AgL fragment (Ba)-4thS fragment (Rf)., namely, a dual-purpose line with light-blue/medium-blue seeds.

The dual-purpose line may have a karyotype of 21 II $(msms)+I_{T4AgL\ fragment\ (Ba)-4thS\ fragment\ (Rf)}.$ The method may specifically include the following steps:

(1) selfing a dual-purpose line 16L6386, harvesting and sowing blue seeds to cultivate plants, selecting male-sterile plants, and screening out male-sterile plants carrying a telosome 4AgL(Ba). through microscopic examination; and selfing the dual-purpose line 16L6386, harvesting and sowing dark-blue seeds to cultivate plants, which are male-fertile plants;

(2) crossing the male-sterile plants screened out in step (1) with the male-fertile plants screened out in step (1), screening out and sowing dark-blue seeds to cultivate plants, and screening out male-sterile plants from plants grown from selfed seeds;

(3) selfing the dual-purpose line 16L6386, harvesting and sowing white seeds to cultivate plants, selecting male-fertile plants, and screening out male-fertile plants carrying a telosome 4thS(Rf). through microscopic examination;

(4) crossing the male-sterile plants screened out in step (2) with the male-fertile plants screened out in step (3), harvesting and sowing blue seeds to cultivate plants, selfing the plants, selecting dark-blue seeds, and screening out double-ditelosomic seeds carrying both a pair of a telosome 4AgL(Ba). and a pair of a telosome 4thS(Rf). through microscopic examination;
(5) subjecting the double-ditelosomic seeds screened out in step (4) to a mutagenesis treatment, and sowing the double-ditelosomic seeds to cultivate plants;
(6) crossing the plants grown from the double-ditelosomic seeds obtained in step (4) as a male parent with white-grained sterile plants (the white-grained sterile plants are male-sterile plants grown from white seeds obtained from selfing of the dual-purpose line 16L6386) as a female parent, harvesting seeds on the female parent plants, selecting blue seeds, subjecting the blue seeds to a mutagenesis treatment, and sowing the blue seeds to cultivate plants;
(7) crossing the plants obtained in step (5) or (6) as a male parent with white-grained sterile plants (the white-grained sterile plants are male-sterile planta grown from white seeds obtained from selfing of the dual-purpose line 16L6386) as a female parent, harvesting seeds on the female parent plants, and screening out blue seeds;
(8) sowing the blue seeds obtained in step (7) to cultivate plants, eliminating male-sterile plants, selfing selected plants, harvesting seeds, and sowing selected seeds to cultivate plants each with both blue seeds and white seeds;
(9) sorting white seeds and blue seeds obtained from selfing of each of the plants screened out in step (8); and
(10) sowing the white seeds and the blue seeds obtained in step (9) to cultivate plants; and if all plants grown from blue seeds of an individual plant are male-fertile plants and all plants grown from white seeds of the individual plant are male-sterile plants (this individual plant is a potential telosome-containing plant), subjecting blue seeds of the individual plant to microscopic examination to obtain a plant line carrying a translocated telosome T4thS fragment (Rf)-4AgL fragment (Ba)., which is a translocation line carrying a translocated telosome T4thS fragment (Rf)-4AgL fragment (Ba)., namely, a dual-purpose line with light-blue/medium-blue seeds.

The dual-purpose line may have a karyotype of 21 II (msms)+$I_{T4thS\ fragment\ (Rf)-4AgL\ fragment\ (Ba)}$.

The method may specifically include the following steps:
(1) propagating a double-ditelosomic seeds carrying both a pair of a translocated telosome T4AgL fragment (Ba)-4BL. and a pair of a telosome 4thS (Rf);
(2) subjecting the double-ditelosomic seeds obtained in step (1) to a mutagenesis treatment, and sowing the double-ditelosomic seeds to cultivate plants;
(3) crossing the plants grown from the double-ditelosomic seeds obtained in step (1) as a male parent with white-grained sterile plants (the white-grained sterile plants are male-sterile plants grown from white seeds obtained from selfing of a dual-purpose line 15L4167) as a female parent, harvesting seeds on the female parent plants, selecting blue seeds, subjecting the blue seeds to a mutagenesis treatment, and sowing the blue seeds to cultivate plants;
(4) crossing the plants obtained in step (2) or (3) as a male parent with white-grained sterile plants (the white-grained sterile plants are male-sterile plants grown from white seeds obtained from selfing of the dual-purpose line 15L4167) as a female parent, harvesting seeds on the female parent plants, and screening out blue seeds;
(5) sowing the blue seeds obtained in step (4) to cultivate plants, eliminating male-sterile plants, selfing selected plants, harvesting seeds, and sowing selected seeds to cultivate plants each with both blue seeds and white seeds;
(6) sorting white seeds and blue seeds obtained from selfing of each of the plants screened out in step (5); and
(7) sowing the white seeds and the blue seeds obtained in step (6) to cultivate plants; and if all plants grown from blue seeds of an individual plant are male-fertile plants and all plants grown from white seeds of the individual plant are male-sterile plants, subjecting blue seeds of the individual plant to microscopic examination to obtain a plant line carrying a translocated telosome T4thS fragment (Rf)-4AgL fragment (Ba)-4BL., which is a translocation line carrying a translocated telosome T4thS fragment (Rf)-4AgL fragment (Ba)-4BL., namely, a dual-purpose line with light-blue/medium-blue seeds.

The dual-purpose line may have a karyotype of 21 II (msms)+$I_{T4thS\ fragment\ (Rf)-4AgL\ fragment\ (Ba)-4BL}$.

The wheat addition line carrying the translocated chromosome T4thS.4AgL can be any wheat with this chromosome form and can be specifically a wheat dual-purpose line obtained by the method in CN200610042629.8 (that is, the dual-purpose line described in line 7 on page 5 of the specification of Chinese Patent Application CN 100420368C, the original dual-purpose line, and a new dual-purpose line). The wheat addition line (dual-purpose line) carrying the translocated chromosome T4thS.4AgL may have a karyotype of 21II (msms)+$I_{T4thS-4AgL}$.

The T4AgL(Ba)-4BL.4BS(Rht3-ms1b) translocation plant line (homozygote) may have a relevant phenotype as follows: a dwarf and male-sterile plant grown from a blue seed.

The double monosomic seed carrying the 4th and the translocated chromosome T4AgL(Ba)-4BL.4BS (Rht3-ms1b) may have a karyotype of 20II+$I_{T4AgL(Ba)-4BL.4BS(Rht3-ms1b)}$+$I_{4th}$.

The wheat 4B substitution line carrying 4th is a wheat 4B substitution line carrying chromosome 4 of *T. thaoudar* (diploid, 2n=14) (N4B). The wheat 4B substitution line carrying 4th may have a relevant phenotype as follows: a blue-grained (a blue-grained gene included does not exhibit xenia), tall, and male-fertile plant.

The white-grained sterile plants of the dual-purpose line 14L6386 are male-sterile plants grown from white seeds obtained from selfing of the dual-purpose line 14L6386.

The dual-purpose line 14L6386 is a blue-grained dual-purpose line obtained by crossing a dual-purpose line 09L6034 (male parent) with a waxy wheat line (female parent) and then selectively breeding (the blue-grained dual-purpose line is waxy wheat, in which the stability of the additional chromosome is poor, but the other agronomic traits are stable).

The dual-purpose line 09L6034 is a blue-grained dual-purpose line obtained by backcrossing a wheat line Zhou88114 (named Zhoumai 11) as a recurrent parent (female parent) with a dual-purpose line T0065-10B-2LB-4 three times and then selectively breeding. The dual-purpose line T0065-10B-2LB-4 is described in CN200610042629.8 (that is, T0065-10B-2LB-4 described in line 14 on page 9 of the specification of Chinese Patent Application CN 100420368C). The T0065-10B-2LB-4 dual-purpose line may have a karyotype of 21II (msms)+$I_{T4thS.4AgL}$, which is a wheat addition line carrying a translocated chromosome T4thS.4AgL.

The dual-purpose line 15L4167 is the addition line carrying the translocated chromosome T4AgL fragment (Ba)-4BL.4thS(Rf).

The dual-purpose line 15L4167 may have a karyotype of 21 II (msms)+$I_{T4AgL\ fragment\ (Ba)-4BL.4thS\ (Rf)}$.

The disomic addition line carrying a pair of a translocated telosome T4AgL fragment (Ba)-4BL. may have a karyotype of 21II (msms)+$II_{T4AgL\ fragment\ (Ba)-4BL.}$ The disomic addition line carrying a pair of the translocated telosome T4AgL fragment (Ba)-4BL. may have a phenotype as follows: seeds are dark-blue, and plants are male-sterile.

The disomic addition line carrying a pair of the telosome 4thS (Rf). may have a karyotype of 21II (msms)+$II_{4thS(Rf)}$.

The disomic addition line carrying a pair of the telosome 4thS (Rf). may have a phenotype as follows: seeds are white, and plants are male-fertile.

The double mono-telosomic seed carrying both a translocated telosome T4AgL fragment (Ba)-4BL. and a telosome 4thS (Rf). may have a karyotype of 21II (msms)+$I_{T4AgL\ fragment\ (Ba)-4BL.}$+$I_{4thSf(Rf)}$.

The dual-purpose line 16L6386 is a wheat addition line carrying a translocated chromosome T4thS.4AgL.

The dual-purpose line 16L6386 is a wheat addition line carrying a translocated chromosome T4thS.4AgL, which is a dual-purpose line obtained through generation selection.

The dual-purpose line 16L6386 is a dual-purpose line cultivated in the Chinese Patent Application (CN200610042629.8), which is obtained through generation selection. The dual-purpose line cultivated in the Chinese Patent Application (CN200610042629.8) is a wheat addition line carrying a translocated chromosome T4thS.4AgL (that is, a wheat line bred from the material T0065-10B-2LB-4 in line 14 on page 9 of Patent Application CN 100420368C).

The wheat dual-purpose addition line carrying the translocated chromosome T4thS.4AgL may have a karyotype of 21II (msms)+$I_{T4thS.4AgL}$.

The double ditelosomic seed carrying both of a pair of a telosome 4AgL(Ba). and a pair of a telosome 4thS (Rf). may have a karyotype of 21II (msms)+$II_{4AgL}$.+$II_{4thS}$.

The double ditelosomic seed carrying both a pair of a translocated telosome T4AgL fragment (Ba)-4BL. and a pair of a telosome 4thS(Rf). may have a karyotype of 21II (msms)+$II_{T4AgL\ fragment\ (Ba)-4BL.}$+$II_{4thS(Rf)}$. Any plant in which a number of white seeds and a number of blue seeds are in a ratio of 2:1 screened out above refers to a plant in which a number of white seeds and a number of blue seeds are in a ratio of about 2:1 in molecular genetics, that is, the ratio is not strictly 2:1 and can go up or down by 5% to 10%.

Any mutagenesis treatment mentioned above can specifically be a treatment with a chemical mutagen DMSO or EMS or a radiation treatment.

Any of the above-mentioned methods may further include the following steps (method 1):

preparing crossing combinations with an elite line and a blue-grained or dark-blue-grained dual-purpose line of a new system, selecting blue seeds from $F_1$-generation seeds, sowing the blue seeds, and according to field performance and indoor seed selection results, screening out an excellent combination in which there is a significant color difference between a blue seed and a white seed or between a blue seed and a red seed; sowing light-blue/medium-blue seeds, and screening out an $F_2$-generation excellent individual plant in which there is a significant color difference between a blue seed and a white seed or between a blue seed and a red seed; separating blue seeds, and white or red seeds of each individual plant, and sowing 82 seeds of each color in 2 rows through 5 cm space planting, with a row length of 2 m and a row spacing of 25 cm; screening out corresponding blue-grained excellent individual plants with prominent agronomic traits when a white-grained or red-grained population in which there are about 25% or 100% of sterile plants; and continuing the selective breeding until a white-grained or red-grained population in which all individual plants are sterile and have stable and consistent agronomic traits is screened out, which is a new dual-purpose line (light-blue/medium-blue seeds). The molecular detection method of the present disclosure (patent application No.: 201810110738.1) can also be used to track and monitor the sterility gene ms1b and purposefully complete the targeted and rapid breeding of next-year multi-generation dual-purpose lines under artificial control conditions. It should be noted that a proportion of white or red seeds of an individual plant or a line screened out in each generation must be greater than or equal to 60%, and a corresponding blue-grained individual plant or line with high outcrossing seed set of white-grained/red-grained sterile plants is screened out.

Any of the above-mentioned methods may further include the following steps (method 2):

the steps are the same as in method 1 except that crosses are prepared between sterile plants of a dual-purpose line and blue-grained or dark-blue-grained plants of another dual-purpose line in a new system; and only blue seeds are sown for each generation.

The present disclosure discloses the creation and use of a two-line hybrid wheat system marked by a blue grain (referred to as a blue-grained two-line hybrid wheat system), where the present disclosure creates alien translocated chromosomes (T4AgL (Ba-containing fragment)-4BL (fragment near centromere).4thS and T4AgL (Ba-containing fragment)-4BL (fragment near centromere).4thS (Rf-containing fragment)) and alien translocated telosomes [T4AgL (Ba-containing fragment)-4thS (Rf-containing fragment), T4thS (Rf-containing fragment)-4AgL (Ba-containing fragment). and T4thS (Rf-containing fragment)-4AgL (Ba-containing fragment)-4BL (fragment near centromere).] of a blue-grained gene, which exhibits xenia and can lead to complete recovery of a recessive GMS gene ms1 on the wheat chromosome 4B; and the present disclosure uses any translocated chromosome or telosome created as an additional monosome for the ms1 homozygous wheat line (dual-purpose line), thereby completing the creation of an improved blue-grained two-line hybrid wheat system.

The different additional alien translocated chromosomes or alien translocated telosomes cannot pair with any chromosome of the common wheat, and can all lead to complete recovery of the ms1 sterility gene series (ms1a, ms1b, ms1c, ms1d . . . ).

In the different additional alien translocated chromosomes or alien translocated telosomes, the restoring gene Rf is derived from chromosome 4 of *Triticum thaoudar* and the blue-grained gene Ba is derived from *Agropyron elongatum*; the translocated chromosome T4AgL (Ba-containing fragment)-4BL (fragment near centromere).4thS has a breakage frequency of 0.5% to 5% at a centromere, where an occurrence frequency of fertile plants in a sterile line is about half of an occurrence frequency of sterile plants in a dual-purpose line; the translocated chromosome T4AgL (Ba-containing fragment)-4BL (fragment near centromere).4thS (Rf-containing fragment) has a breakage frequency of 0% to 1% at a centromere, where an occurrence frequency of fertile plants in a sterile line is about half of an occurrence frequency of sterile plants in a dual-purpose line; a separation frequency of two target genes in the telosome T4AgL (Ba-containing fragment)-4thS (Rf-containing fragment) is 0% to 1%, where an occurrence frequency of fertile plants in a sterile line is 0% to 0.5% and no sterile plants occur in a blue-grained population; and a separation frequency of two target genes in the telosomes T4thS (Rf-containing fragment)-4AgL (Ba-containing fragment). and T4thS (Rf-containing fragment)-4AgL (Ba-containing fragment)-4BL (fragment near centromere) is 0% to 1%, where no fertile plants occur in a sterile line, and an occurrence frequency of sterile plants in a dual-purpose line is 0% to 1%.

Proportions of seeds with different colors produced from selfing of different dual-purpose lines are different, for example, a proportion of a white or red seed (sterile line) varies by 55% to 85%; a proportion of a light-blue/medium-blue seed (monosomic addition, dual-purpose line) is 15% to 40%, and a proportion of a dark-blue seed (ditelosomic addition) is 2% to 6%, where a sterile line seed is used for the production of a hybrid, a dual-purpose line seed is used for the propagation of a sterile line and a dual-purpose line, and a dark-blue seed (ditelosomic addition) is eliminated, used as a parent, or used for purification and rejuvenation of a dual-purpose line.

In order to accelerate the industrialization of the blue-grained two-line hybrid wheat system, the stability of dual-purpose lines (sterile lines) used in the breeding of an approved hybrid and a strong-dominant combination with the method for breeding two-line hybrid wheat marked by blue grains (CN200610042629.8) needs to be further improved, a newly-created alien translocated chromosome or telosome is used to replace the original additional chromosome, and these dual-purpose lines include 08L5070, 12L8012, 12L8015, 12L8016, 18L7077, and the like. During this process, a target sterile line as a recurrent parent can be obtained by backcrossing continuously for more than 6 times with blue-grained or dark-blue-grained homozygous plants of a dual-purpose line from one of the new improved systems in 2 to 3 years under an artificial control environment, and the same sterile line in a new system as the original one is screened out, thereby the replacement of an additional translocated chromosome or telosome is achieved. The above sterile lines such as 08L5070 and 12L8012 have been backcrossed for 4 times to obtain a new system. In the same way, any dual-purpose line transferring into a new system by the replacement of a new translocated chromosome or telosome can be achieved.

The present disclosure also provides a (translocated chromosome) including 4AgL fragment (Ba), 4BL, centromere, and 4thS (Rf).

The present disclosure also provides a (translocated chromosome) including 4AgL fragment (Ba), 4BL, centromere, and 4thS fragment (Rf).

The present disclosure also provides a (translocated telosome) including 4AgL fragment (Ba), 4thS fragment (Rf), and centromere.

The present disclosure also provides a (translocated telosome) including 4thS fragment (Rf), 4AgL fragment (Ba), and centromere.

The present disclosure also provides a (translocated telosome) including 4thS fragment (Rf), 4AgL fragment (Ba)-4BL, and centromere.

4AgL represents the long arm of chromosome 4Ag derived from *Agropyron elongatum* and has a gene Ba. 4AgL can also be represented by 4AgL(Ba). A 4AgL fragment retaining the gene Ba is represented by 4AgL fragment (Ba).

4th represents chromosome 4 of *T. thaoudar*.

4thS represents the short arm of 4th and includes a gene for restoring male fertility (gene Rf). 4thS can also be represented by 4thS(Rf). A 4thS fragment retaining the gene Rf is represented by 4thS fragment (Rf).

4B represents chromosome 4 of a chromosome set B of the hexaploid common wheat (*T. aestivum*).

4BS represents the short arm of 4B.

4BL represents the long arm of 4B.

4BS (Rht3-ms1b) represents 4BS with the linkage of an Rht3 gene and an ms1b gene. The Rht3 gene is a dwarfing gene (derived from Nainari Rht3). The ms1b gene is a male sterility gene (derived from a Probus mutant).

"." represents a centromere. T represents a translocated chromosome or telosome (namely, a chromosome arm with a centromere). II represents a bivalent. I represents a monovalent. N4B represents the deletion of chromosome 4B, namely, no chromosome 4B.

Herein, the semi-dwarf and male-sterile wheat carrying ms1b-Rht3 is any wheat with the traits and chromosome form, such as a semi-dwarf and male-sterile wheat carrying ms1b-Rht3 obtained by the method described in CN200610042629.8 (that is, ms-Rht3/Ms-rht3-containing (semi-dwarf) wheat in line 13 on page 7 of the specification of Patent Application CN 100420368C).

Under the guidance of theory and practice, the present disclosure makes full use of the traditional biological technology, chromosome engineering technology, and crop genetic breeding method based on germplasm materials accumulated early to create a stable alien translocated chromosome or telosome with the close linkage of an alien restoring gene and a blue-grained gene, such as to achieve the purpose of improving a blue-grained two-line hybrid wheat system.

Based on the Chinese Patent Application (CN200610042629.8), the present disclosure improves the stability of an additional translocated chromosome during production of a sterile line, and creates alien translocated chromosomes (T4AgL (Ba-containing fragment)-4BL (fragment near centromere).4thS and T4AgL (Ba-containing fragment)-4BL (fragment near centromere).4thS (Rf-containing fragment)) and alien translocated telosomes (T4AgL (Ba-containing fragment)-4thS (Rf-containing fragment), T4thS (Rf-containing fragment)-4AgL (Ba-containing fragment). and T4thS (Rf-containing fragment)-4AgL (Ba-containing fragment)-4BL (fragment near centromere).) of a blue-grained gene Ba and an exogenous restoring gene Rf, which exhibit xenia and dose-response and can lead to complete recovery of a recessive GMS gene ms1. The present disclosure uses any created translocated chromosome or translocated telosome as an additional monosome for an ms1 homozygous line (namely, a dual-purpose line, which has medium-blue and light-blue seeds) to complete the improvement of a blue-grained two-line hybrid wheat system.

White/red seeds (sterile line) and blue seeds are obtained by selfing a dual-purpose line, and white/red seeds (sterile line), light/medium-blue seeds (dual-purpose line), and dark-blue seeds are separated by a color sorter, where a sterile line is used for hybrid seed production, a light/medium-blue seed (a dual-purpose line) is used for the propagation of a sterile line and the dual-purpose line again, and dark-blue seeds are eliminated, used as a parent to breed a new sterile line, or used for purification and rejuvenation of a dual-purpose line. Different translocated chromosomes or telosomes can be replaced with each other as required to meet the requirements of purity and stability of sterile lines under different genetic backgrounds. The present disclosure has characteristics such as rapid breeding of sterile lines, low production cost of hybrid seeds, and strong heterosis, and is more stable and reliable than the method for breeding two-line hybrid wheat marked by Chinese Patent Application (CN200610042629.8).

DETAILED DESCRIPTION

Figure 1:
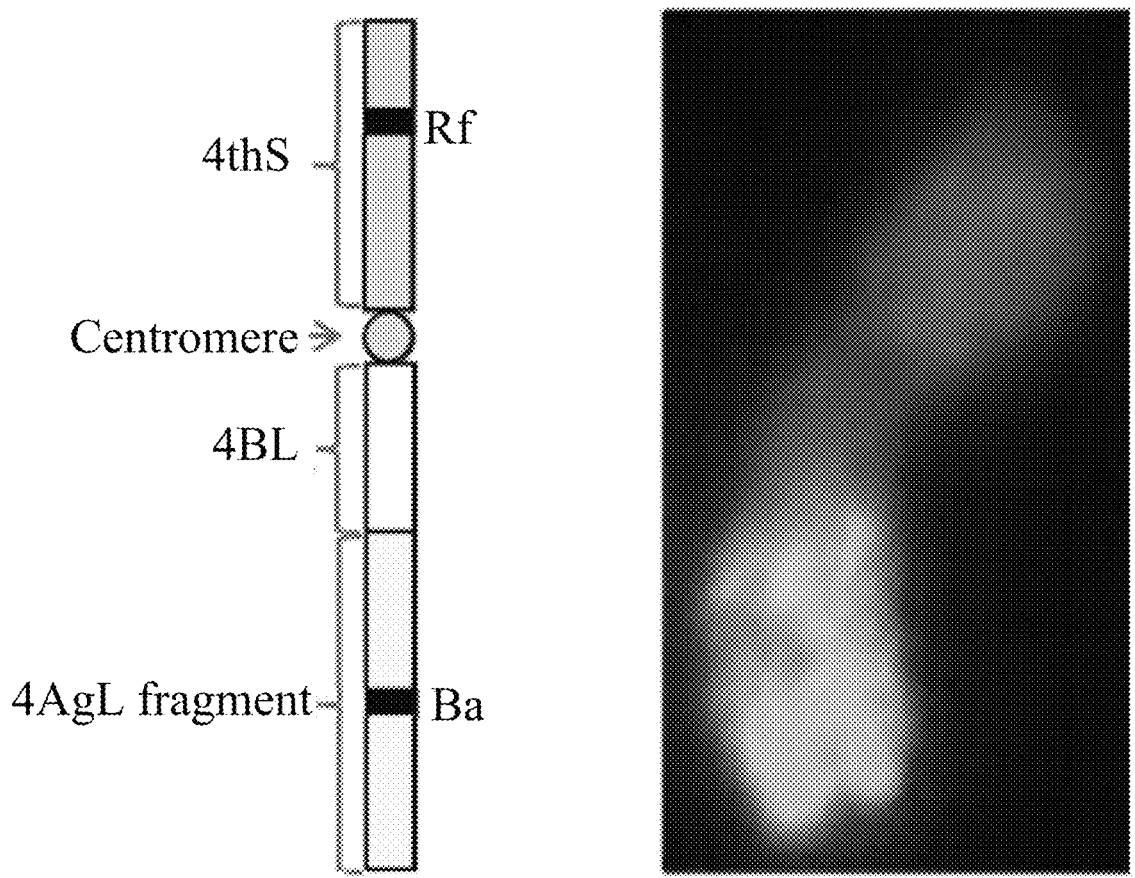
FIG. 1 shows a schematic diagram and an FISH image of the translocated chromosome T4AgL fragment (Ba)-4BL.4thS (Rf) (left: schematic diagram; and right: FISH image).

The present disclosure will be described in further detail below with reference to specific examples. The examples given are only for the purpose of illustrating the present disclosure, and are not intended to limit the scope of the present disclosure. The examples provided below can serve as a guide for further improvement by those of ordinary skill in the art, and are not intended to limit the present disclosure in any way.

Unless otherwise specified, the experimental methods described in the following examples are all conventional methods. The methods shall be conducted in accordance with the techniques or conditions described in the literature in the art or in accordance with the product specification. The materials, reagents, and the like used in the following examples are all commercially available, unless otherwise specified. Unless otherwise specified, three replicate experiments are set for each of the quantitative tests in the following examples, and results are averaged.

4AgL represents a long arm of chromosome 4Ag of *Agropyron elongatum*, and has a gene Ba, which is a blue-grained gene that exhibits xenia and dose-response and is a dominant gene. A seed in which the endosperm and aleurone layer each have 3 copies of gene Ba is dark-blue, a seed in which the endosperm and aleurone layer each have 2 copies of gene Ba is medium-blue, a seed in which the endosperm and aleurone layer each have 1 copy of gene Ba is light-blue, and a seed in which the endosperm and aleurone layer each do not have the gene Ba is white or red. 4AgL can also be represented by 4AgL(Ba). A 4AgL fragment retaining the gene Ba is represented by 4AgL fragment (Ba).

4th represents chromosome 4 of *T. thaoudar*.

4thS represents a short arm of 4th and includes a gene for restoring male fertility (gene Rf). 4thS can also be represented by 4thS(Rf). A 4thS fragment retaining the gene Rf is represented by 4thS fragment (Rf).

4B represents chromosome 4 of a chromosome set B of the hexaploid common wheat (*T. aestivum*).

4BS represents the short arm of 4B.

4BL represents the long arm of 4B.

4BS (Rht3-ms1b) represents 4BS with the linkage of an Rht3 gene and an ms1b gene. A gene Rht3 is a dwarfing gene (derived from Nainari Rht3), which is a dominant gene. A plant with 2 copies of gene Rht3 is a dwarf plant, a plant with 1 copy of gene Rht3 is a semi-dwarf plant, and a plant without the gene Rht3 is a tall plant. The ms1b gene is a male sterility gene (derived from a Probus mutant), which is a recessive gene.

"." represents a centromere. T represents a translocated chromosome or telosome (namely, a chromosome arm with a centromere). II represents a bivalent. I represents a monovalent. N4B represents the deletion of chromosome 4B, namely, no chromosome 4B.

In the examples, "non-blue" (including "white" or "red") and "blue" (including "light-blue," "medium-blue," or "dark-blue") refer to color traits of seeds. In the examples, "dwarf," "semi-dwarf," and "tall" refer to height traits of plants. In the examples, "fertile" and "sterile" refer to male reproductive traits of plants. For example, a plant with blue-seed, dwarf-stem, and sterility traits refers to a dwarf and male-sterile plant grown from a blue seed.

Unless otherwise specified, male-sterile plants are used as a female parent and another parent plants are used as a male parent for crossing in the examples.

Example 1 Creation of a Translocated Chromosome T4AgL Fragment (Ba)-4BL.4thS (Rf)

1. A translocated chromosome T4AgL(Ba)-4BL.4BS (Rht3-ms1b) was acquired.

(1) 4AgL(Ba) was recombined into 4B to obtain a translocated chromosome T4AgL(Ba)-4BL.4BS.

(2) White-grained sterile plants of a dual-purpose line 06L6109-3 were crossed with a wheat plant carrying a translocated chromosome T4AgL(Ba)-4BL.4BS (a tall and male-fertile wheat plants grown from blue seeds), and dwarf and male-sterile plantz grown from blue seeds were screened out.

The white-grained sterile plants of the dual-purpose line 06L6109-3 were dwarf and male-sterile plantx grown from white seeds obtained from selfing of the dual-purpose line 06L6109-3.

The dual-purpose line 06L6109-3 was an Rht3-ms1b-containing blue-grained dual-purpose line obtained by crossing an Rht3-ms1b-containing semi-dwarf and male-sterile wheat plants grown from white seeds with a dual-purpose line obtained by the method in CN200610042629.8 and then selectively breeding. The dual-purpose line obtained by the method in CN200610042629.8 had a karyotype of 21 II (msms)+$I_{T4thS.4AgL}$, and was a wheat addition line carrying a translocated chromosome T4thS.4AgL.

(3) Dwarf plants grown from blue seeds were screened out, which were a plant line carrying the translocated chromosome T4AgL(Ba)-4BL.4BS(Rht3-ms1b) and was called a T4AgL(Ba)-4BL.4BS (Rht3-ms1b) translocation line. The T4AgL(Ba)-4BL.4BS(Rht3-ms1b) translocation plant line (homozygote) had a relevant phenotype as follows: dwarf and male-sterile plants grown from blue seeds.

(4) The plants screened out in step (3) were crossed with wheat plants carrying a translocated chromosome T4AgL(Ba)-4BL.4BS (tall and male-fertile wheat plants grown from blue seeds), plants obtained from the crossing were selfed, and resulting seeds were stored, such that dwarf and male-sterile plants similar to those in step (3) were continuously obtained.

2. The T4AgL(Ba)-4BL.4BS (Rht3-ms1b) translocation plant line (homozygote) was crossed with a wheat 4B substitution line carrying 4t^h to obtain 500 or more double monosomic seeds carrying the 4t^h and the translocated chromosome T4AgL(Ba)-4BL.4BS (Rht3-ms1b). The double monosomic seed had a karyotype of 20II+ $I_{T4AgL(Ba)-4BL.4BS(Rht3-ms1b)}+I_{4th}$.

The wheat 4B substitution line carrying 4t^h was a wheat 4B substitution line carrying a pair of chromosome 4 of *T. thaoudar* (diploid, 2n=14) (N4B). The wheat 4B substitution line carrying 4t^h had a relevant phenotype as follows: blue-grained (a blue-grained gene included did not exhibit xenia), tall, and male-fertile plants.

3. The double monosomic seeds obtained in step 2 were sown to cultivate plants, the plants were selfed, dark-blue seeds were selected and sown, and tall and male-fertile plants were screened out.

4. The plants screened out in step 3 were crossed with white-grained sterile plants of a dual-purpose line 14L6386, a total of 561 crossing combinations were prepared and numbered, and a crossing combination leading to a blue seed was screened out (a blue-grained gene on the chromosome 4t^h was eliminated here).

The white-grained sterile plants of the dual-purpose line 14L6386 were male-sterile plants grown from white seeds obtained from selfing of the dual-purpose line 14L6386.

The dual-purpose line 14L6386 was a blue-grained dual-purpose line obtained by crossing a dual-purpose line 09L6034 (male parent) with a waxy wheat line (female parent) and then selectively breeding (the blue-grained dual-purpose line was waxy wheat, in which the stability of the additional chromosome was poor, but the other agronomic traits were stable).

The dual-purpose line 09L6034 was a blue-grained dual-purpose line obtained by backcrossing a wheat line Zhou88114 (named Zhoumai 11) as a recurrent parent (female parent) with a dual-purpose line T0065-10B-2LB-4 for three times and then selectively breeding. The dual-purpose line T0065-10B-2LB-4 was described in CN200610042629.8. The T0065-10B-2LB-4 dual-purpose line had a karyotype of 21II (msms)+$I_{T4thS.4AgL}$, and was a wheat addition line carrying a translocated chromosome T4thS.4AgL.

5. According to a screening result in step 4, blue seeds of different crossing combinations were sequentially sown to cultivate plants. If plants grown from all seeds of a corresponding crossing combination were male-fertile plants, the plants grown from the seeds constituted a potential translocation line. A total of 35 potential translocation lines were obtained, namely 14T1, 14T2, . . . , 14T34, and 14T35.

6. Each of the 35 potential translocation lines obtained in step (5) was selfed, seeds were harvested, blue seeds were classified into a group, and white seeds were classified into a group; the blue seeds (100 seeds/potential translocation line) and the white seeds (100 seeds/potential translocation line) were sown separately to cultivate plants; and if all individual plants grown from the blue seeds were male-fertile plants and all individual plants grown from the white seeds were male-sterile plants, the male-fertile plants grown from the blue seeds were subjected to FISH identification, and individual plants carrying a translocated chromosome T4AgL fragment (Ba)-4BL.4thS (Rf) were screened out, which constituted a T4AgL fragment (Ba)-4BL.4thS (Rf) translocation line. A total of 5 translocation lines meeting the requirements were obtained, namely 14T9, 14T12, 14T21, 14T31, and 14T34. A less stable translocation line 14T35 was also obtained and would be used in Example 2.

Figure 2:
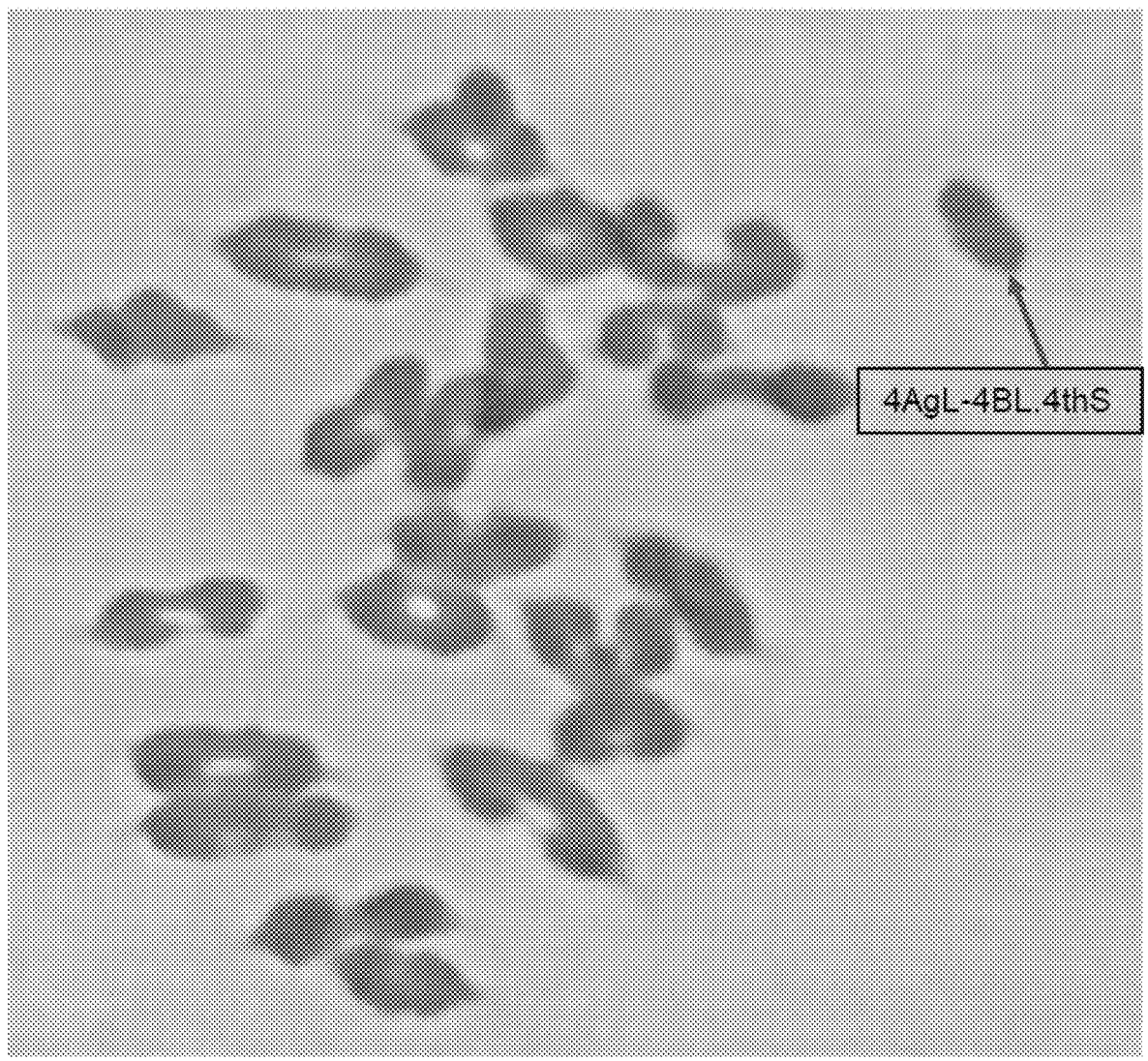
FIG. 2 is a karyogram of a plant of an addition line: 21II (msms)+$I_{T4AgL\ fragment\ (Ba)\text{-}4BL.4thS(Rf)}$.

7. From selfed progeny of the 5 translocation lines obtained in step 6, a plant line in which a number of white seeds and a number of blue seeds were in a ratio of about 2:1 was screened out, which was an addition line carrying the translocated chromosome T4AgL fragment (Ba)-4BL.4thS (Rf) (a dual-purpose line). The addition line had a karyotype of 21 II (msms)+$I_{T4AgL\ fragment\ (Ba)}$-4BL.4thS(Rf). A schematic diagram and an FISH image of the translocated chromosome T4AgL fragment (Ba)-4BL.4thS (Rf) were shown in FIG. 1. A karyogram of the addition line was shown in FIG. 2.

The obtained addition line was cultivated on a large scale, and an occurrence frequency of male-sterile plants in the blue-grained population and an occurrence frequency of male-fertile plants in the white-grained population were investigated. The occurrence frequency of male-sterile plants in the blue-grained population was 0.5% to 5%; and the occurrence frequency of male-fertile plants in the white-grained population was 0.2% to 3%. 1,000 or more plants were tested for each population.

Example 2 Creation of a Translocated Chromosome T4AgL Fragment (Ba)-4BL.4thS Fragment (Rf)

1. An Rf gene-containing telosome addition line and a Ba gene-containing telosome addition line were created.

With the translocation line 14T35 obtained in Example 1, generation selection was conducted to obtain a dual-purpose line 15L4167 (in which the stability of the additional chromosome was poor, but the other agronomic traits were stable). The dual-purpose line 15L4167 was an addition line carrying the translocated chromosome T4AgL fragment (Ba)-4BL.4thS(Rf) (a dual-purpose line). The dual-purpose line 15L4167 had a karyotype of 21 II (msms)+$I_{T4AgL\ fragment\ (Ba)-4BL.4thS(Rf)}$.

The dual-purpose line 15L4167 was selfed, and then male-sterile plants grown from blue seeds were screened out, which were plants carrying a translocated telosome T4AgL fragment (Ba)-4BL.; the male-sterile plants were crossed with a dark-blue-grained fertile plants (the dark-blue-grained fertile plants were male-fertile plants grown from dark-blue seeds obtained from selfing of the dual-purpose line 15L4167, and seeds produced after selfing of the dark-blue-grained fertile plants were all blue seeds), and male-fertile plants grown from dark-blue seeds were screened out and selfed; and male-sterile plants were screened out from plants grown from selfed seeds, and microscopic screening was further conducted to obtain an addition line carrying a translocated telosome T4AgL fragment (Ba)-4BL. The addition line had a karyotype of 21 II (msms)+$I_{T4AgL\ fragment\ (Ba)-4BL}$. The addition line had a phenotype as follows: seeds were medium-blue, and plants were male-sterile.

The dual-purpose line 15L4167 was selfed, male-fertile plants grown from white seeds obtained from the selfing (which were plants carrying a telosome 4thS (Rf).) were selected, and microscopic screening was further conducted to obtain an addition line carrying a telosome 4thS (Rf). The addition line had a karyotype of 21 II (msms)+$I_{4thS\ Rf)}$. The addition line had a phenotype as follows: seeds were white, and plants were male-fertile.

2. The addition line carrying the telosome 4thS (Rf). as a male parent was crossed with the addition line carrying the translocated telosome T4AgL fragment (Ba)-4BL. as a female parent to obtain 500 or more double-mono-telosomic seeds each carrying the translocated telosome T4AgL fragment (Ba)-4BL. and the telosome 4thS (Rf). The double-mono-telosomic seeds had a karyotype of 21II (msms)+$I_{T4AgL\ fragment\ (Ba)-4\ BL.}$+$I_{4thS\ (Rf).}$.

3. Male and female parent plants were cultivated with the seeds obtained in step 2 as a male parent and white seeds (the white seeds were obtained from selfing of the dual-purpose line 15L4167) as a female parent, the male and female parent plants were crossed (the double-mono-telosomic seeds obtained in step 2 and the white seeds were sown alternately in a row ratio of 2:(2-4) to cultivate plants, and then artificial supplementary pollination was conducted at a flowering stage), and blue seeds were screened out from seeds obtained from the female parent plants.

4. The blue seeds obtained in step 3 were sown to cultivate plants, male-sterile plants were eliminated, male-fertile plants were harvested and subjected to indoor seed selection, and selected seeds were sown to cultivate plants each with both blue seeds and white seeds.

5. A total of 1,480 individual plants were screened out in step 4, and white seeds and blue seeds of each of the individual plants were screened out.

6. The white seeds and the blue seeds obtained in step 5 were sown (80 white seeds and 80 blue seeds per individual plant) to cultivate plants; and if all plants grown from blue seeds of an individual plant were male-fertile plants and all plants grown from white seeds of the individual plant were male-sterile plants, light-blue seeds of the individual plant were subjected to microscopic examination to obtain a translocation line carrying a translocated chromosome T4AgL fragment (Ba)-4BL.4thS fragment (Rf), which was also known as a dual-purpose line.

A total of 2 individual plants were obtained from the field selection, numbered 15yi 3357 and 15yi 3359, and subjected to microscopic examination, and it was found that 15yi 3357 had a translocated chromosome T4AgL fragment (Ba)-4BL.4thS fragment (Rf).

Figure 3:
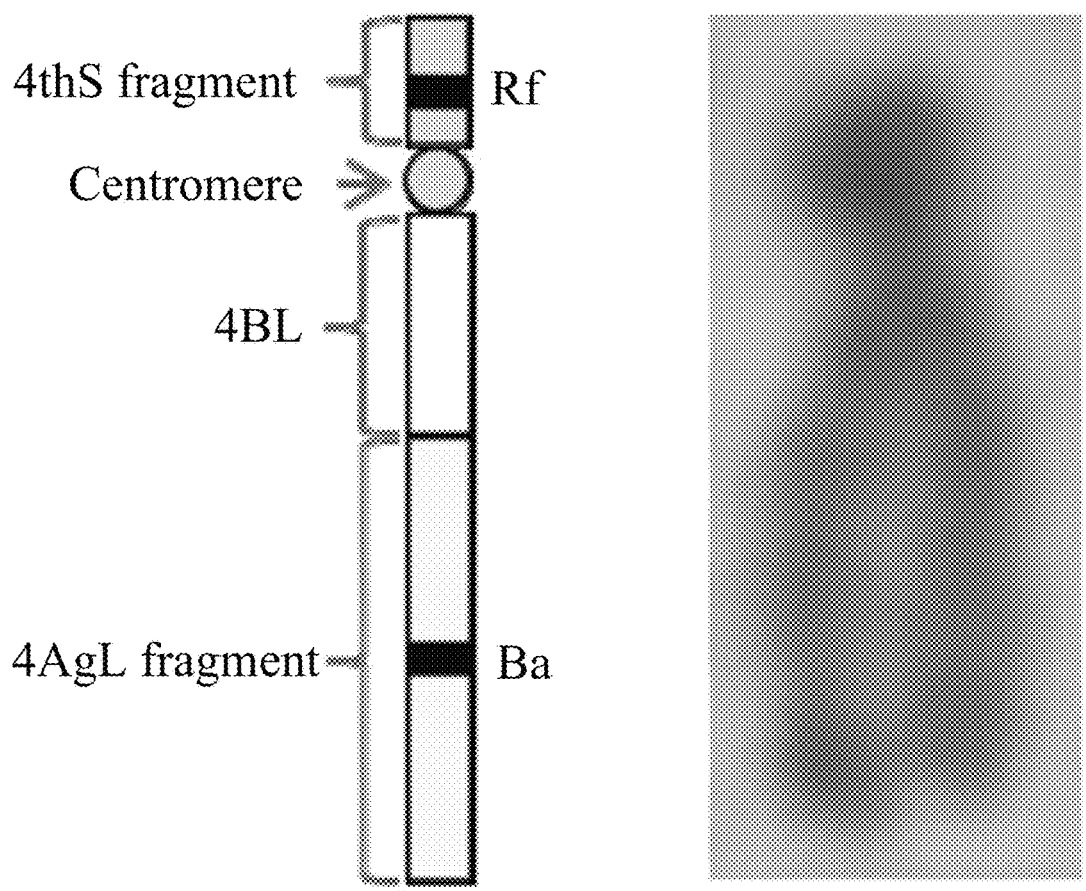
FIG. 3 shows a schematic diagram and a chromosome image of the translocated chromosome T4AgL fragment (Ba)-4BL.4thS fragment (Rf) (left: schematic diagram; and right: chromosome image).

A schematic diagram of the translocated chromosome T4AgL fragment (Ba)-4BL.4thS fragment (Rf) was shown in FIG. 3.

The obtained addition line was cultivated on a large scale, and an occurrence frequency of male-sterile plants in the blue-grained population and an occurrence frequency of male-fertile plants in the white-grained population were investigated. A breakage frequency of the translocated chromosome T4AgL fragment (Ba)-4BL.4thS fragment (Rf) at a centromere was less than 2%, and an occurrence frequency of fertile plants in the sterile line was about half of an occurrence frequency of sterile plants in the dual-purpose line. 1,000 or more plants were tested for each population.

Example 3 Creation of Translocated Telosomes T4AgL Fragment (Ba)-4thS Fragment (Rf)., T4thS Fragment (Rf)-4AgL Fragment (Ba)., or T4thS Fragment (Rf)-4AgL Fragment (Ba)-4BL I. Creation of Translocated Telosomes T4AgL Fragment (Ba)-4thS Fragment (Rf). and T4thS Fragment (Rf)-4AgL Fragment (Ba).

1. Acquisition of a double-ditelosomic addition line (1) The dual-purpose line cultivated in the Chinese Patent Application (CN200610042629.8) had a karyotype of 21II (msms)+$I_{T4thS-4AgL}$, and was a wheat addition line carrying a translocated chromosome T4thS.4AgL (a dual-purpose line 16L6386).

(2) The dual-purpose line 16L6386 was selfed, blue seeds were harvested and sown to cultivate plants, male-sterile plants were selected, and male-sterile plants carrying a telosome 4AgL(Ba). were screened out through microscopic examination.

(3) The dual-purpose line 16L6386 was selfed, and dark-blue seeds were harvested and sown to cultivate plants, which were male-fertile plants.

(4) The plants screened out in step (2) was crossed with the plants screened out in step (3), dark-blue seeds were screened out and sown to cultivate plants, and male-sterile plants were screened out from selfed progeny of the plants. With the dark-blue seeds screened out above, enough seeds were obtained through self-propagation (the seeds were all dark-blue seeds).

(5) The dual-purpose line 16L6386 was selfed, white seeds were harvested and sown to cultivate plants, male-fertile plants were selected, and male-fertile plants carrying a telosome 4thS(Rf). were screened out through microscopic examination. Enough seeds were obtained through self-propagation for later use.

(6) The male-sterile plants screened out in step (4) were crossed with the male-fertile plants screened out in step (5), blue seeds were harvested and sown to cultivate plants, the plants were selfed, dark-blue seeds were selected, and double-ditelosomic seeds carrying both a pair of a telosome 4AgL(Ba). and a pair of a telosome 4thS(Rf). were screened out through microscopic examination, which were a double-ditelosomic addition line. The double-ditelosomic seed had a karyotype of 21II (msms)+$II_{4AgL(Ba)}$+$II_{4thS(Rf)}$. Enough seeds (dark-blue seeds) were obtained through self-propagation for later use.

2. The double-ditelosomic seeds obtained in step 1 were subjected to a treatment with a chemical mutagen DMSO or EMS or a radiation treatment, and then sown to cultivate plants.

3. The plants grown from the double-ditelosomic seeds obtained in step (1) as a male parent were crossed with white-grained sterile plante (the white-grained sterile plante were male-sterile plants grown from white seeds obtained from selfing of the dual-purpose line 16L6386) as a female parent, seeds on the female parent plants were harvested, and blue seeds were selected, subjected to a treatment with a chemical mutagen DMSO or EMS or a radiation treatment, and then sown to cultivate plants.

4. The plants obtained in step 2 or 3 as a male parent was crossed with a white-grained sterile plants (the white-grained sterile plants were male-sterile plants grown from white seeds obtained from selfing of the dual-purpose line 16L6386) as a female parent, seeds on the female parent plants were harvested, and blue seeds were screened out.

5. The blue seeds obtained in step 4 were sown to cultivate plants, male-sterile plants were eliminated, a total of 26,567 individual plants were selected and selfed, and seeds were harvested and sown to cultivate plants each with both blue seeds and white seeds.

6. White seeds and blue seeds obtained from selfing of each of the plants screened out in step 5 were collected separately.

7. The white seeds and the blue seeds obtained in step 6 were sown (100 white seeds and 100 blue seeds were sorted for each individual plant) to cultivate plants; and if all plants grown from blue seeds of an individual plant were male-fertile plants and all plants grown from white seeds of the individual plant were male-sterile plants (this individual plant was a potential telosome-containing plant), blue seeds of the individual plant were subjected to microscopic examination to obtain a line carrying a translocated telosome T4AgL fragment (Ba)-4thS fragment (Rf). or a translocated telosome T4thS fragment (Rf)-4AgL fragment (Ba)., which was a dual-purpose line with light-blue/medium-blue seeds. A total of 9 lines were obtained, namely 20DT1, 20DT2, . . . , 20DT9. Lines grown from the blue seeds in which there was no male-sterile plant included translocation lines each carrying a translocated telosome T4AgL fragment (Ba)-4thS fragment (Rf)., 20DT1, 20DT3, 20DT7, and 20DT9. Lines grown from the white seeds in which there was no male-fertile plant included translocation lines each carrying a translocated telosome T4thS fragment (Rf)-4AgL fragment (Ba)., 20DT2, 20DT4, 20DT5, 20DT6, and 20DT8.

Figure 4:
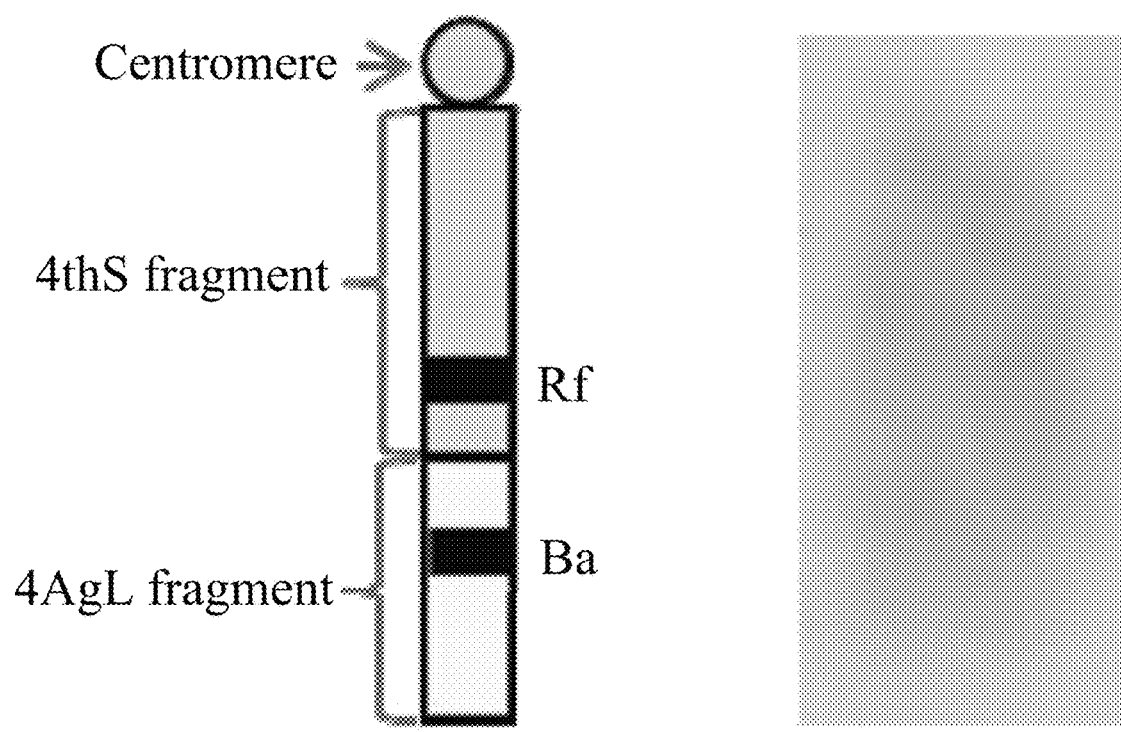
FIG. 4 shows a schematic diagram and a telosome image of the translocated telosome T4AgL fragment (Ba)-4thS fragment (Rf). (left: schematic diagram; and right: telosome image).

A schematic diagram of the translocated telosome T4AgL fragment (Ba)-4thS fragment (Rf). was shown in FIG. 4.

Figure 5:
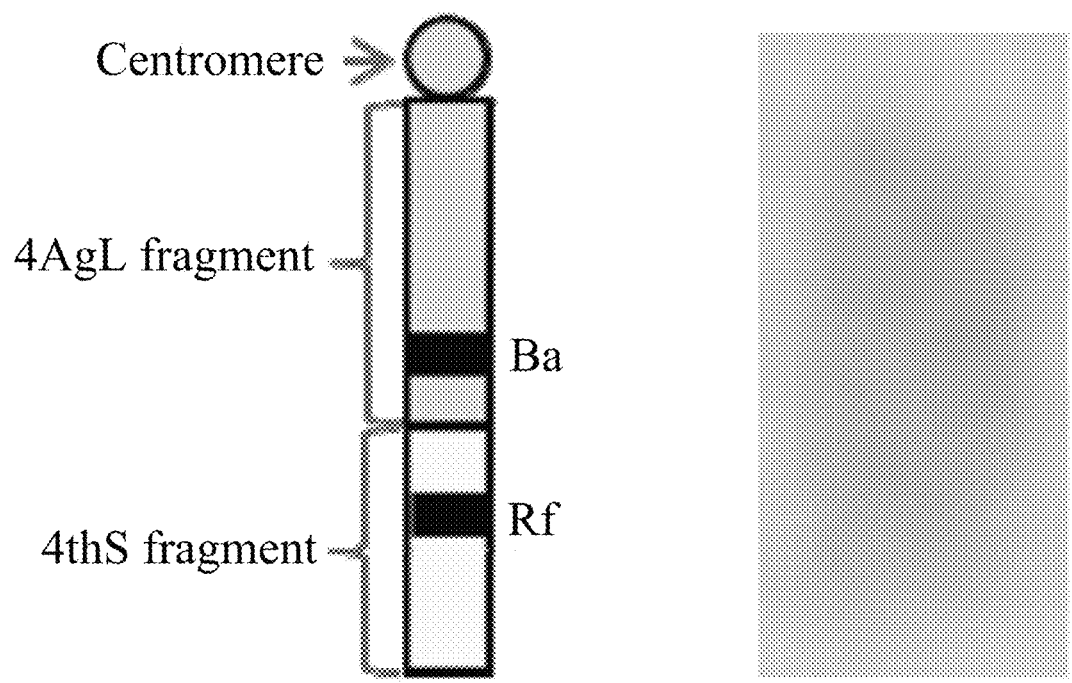
FIG. 5 shows a schematic diagram and a telosome image of the translocated telosome T4thS fragment (Rf)-4AgL fragment (Ba). (left: schematic diagram; and right: telosome image).

A schematic diagram of the translocated telosome T4thS fragment (Rf)-4AgL fragment (Ba). was shown in FIG. 5.

II. Creation of a Translocated Telosome T4thS Fragment (Rf)-4AgL Fragment (Ba)-4BL.

1. A double-ditelosomic seeds carrying both a pair of a translocated telosome T4AgL fragment (Ba)-4BL and a pair of a telosome 4thS (Rf). obtained in Example 2 were propagated.

2. The double-ditelosomic seeds obtained in step 1 were subjected to a treatment with a chemical mutagen DMSO or EMS or a radiation treatment, and then sown to cultivate plants.

3. The plants grown from the double-ditelosomic seeds obtained in step (1) as a male parent were crossed with white-grained sterile plants (the white-grained sterile plants were male-sterile plants grown from white seeds obtained from selfing of the dual-purpose line 15L4167) as a female parent, seeds on the female parent plants were harvested, and blue seeds were selected, subjected to a treatment with a chemical mutagen DMSO or EMS or a radiation treatment, and then sown to cultivate plants.

4. The plants obtained in step 2 or 3 as a male parent were crossed with a white-grained sterile plants (the white-grained sterile plants were male-sterile plants grown from white seeds obtained from selfing of the dual-purpose line 15L4167) as a female parent, seeds on the female parent plants were harvested, and blue seeds were screened out.

5. The blue seeds obtained in step 4 were sown to cultivate plants, male-sterile plants were eliminated, selected plants were selfed, seeds were harvested, and plants each with both blue seeds and white seeds were screened out.

6. White seeds and blue seeds obtained from selfing of each of the plants screened out in step 5 were collected separately.

7. The white seeds and the blue seeds obtained in step 6 were sown (100 white seeds and 100 blue seeds were sorted for each individual plant) to cultivate plants; and if all plants grown from blue seeds of an individual plant were male-fertile plants and all plants grown from white seeds of the individual plant were male-sterile plants, blue seeds of the individual plant were subjected to microscopic examination to obtain a plant line carrying a translocated telosome T4thS fragment (Rf)-4AgL fragment (Ba)-4BL, which was a translocation line carrying a translocated telosome T4thS fragment (Rf)-4AgL fragment (Ba)-4BL. A translocation line 21DT1 was obtained.

Figure 6:
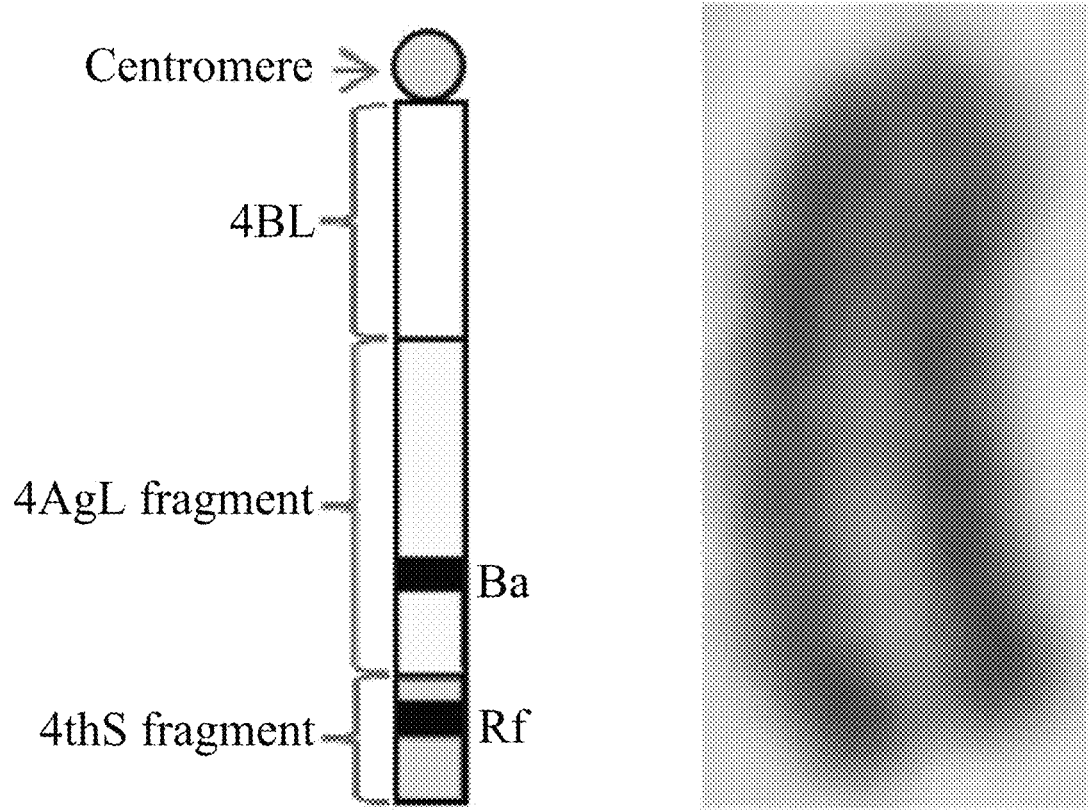
FIG. 6 shows a schematic diagram and a telosome image of the translocated telosome T4thS fragment (Rf)-4AgL fragment (Ba)-4BL (left: schematic diagram; and right: telosome image).

A schematic diagram of the translocated telosome T4thS fragment (Rf)-4AgL fragment (Ba)-4BL was shown in FIG. 6.

III. Performance of Translocated Telosomes T4AgL Fragment (Ba)-4thS Fragment (Rf)., T4thS Fragment (Rf)-4AgL Fragment (Ba)., or T4thS Fragment (Rf)-4AgL Fragment (Ba)-4BL.

A separation frequency of two target genes in the translocated telosome T4AgL fragment (Ba)-4thS fragment (Rf). was 0% to 1%. An occurrence frequency of fertile plants in the sterile line was 0% to 0.5%, and there was no sterile plant in the blue-grained population. A separation frequency of two target genes in the translocated telosomes T4thS fragment (Rf)-4AgL fragment (Ba). and T4thS fragment (Rf)-4AgL fragment (Ba)-4BL. was 0% to 1%. There was no fertile plant in the sterile line, and an occurrence frequency of sterile plants in the dual-purpose line was 0% to 1%.

Proportions of seeds with different colors produced from selfing of different dual-purpose lines were different, for example, a proportion of a white or red seed (sterile line) varied by 55% to 85%; a proportion of a light-blue/medium-blue seed (dual-purpose line) was 15% to 40%, and a proportion of a dark-blue seed (ditelosomic addition) was 2% to 6%, where a sterile line was used for the production of a hybrid seed, a dual-purpose line was used for the propagation of a sterile line and a dual-purpose line again, and a dark-blue seed was eliminated, used as a parent, or used for purification and rejuvenation of a dual-purpose line.

Example 4 Breeding Methods of New Dual-Purpose Lines (Sterile Lines)

Figure 7:
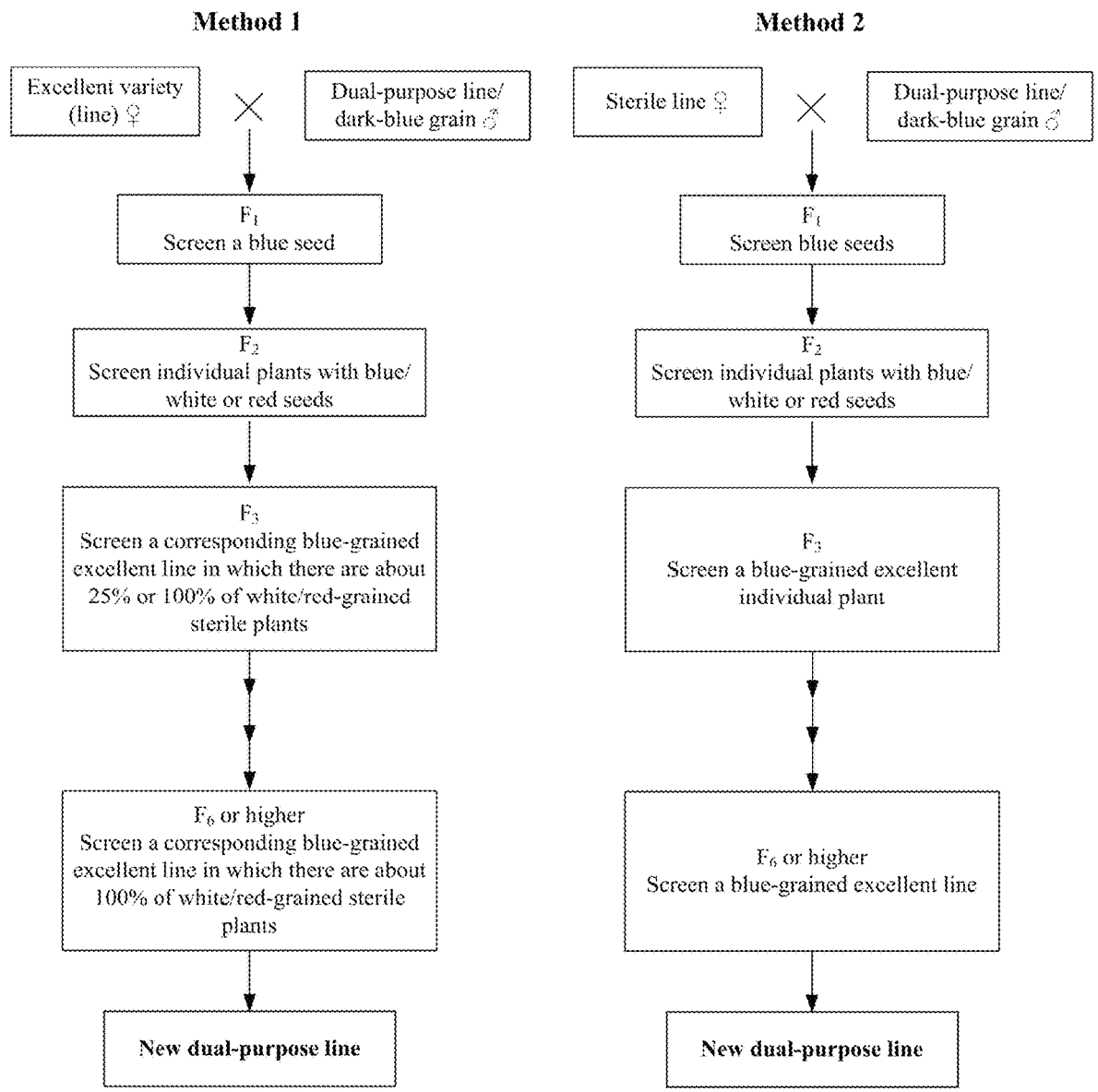
FIG. 7 is a schematic diagram of a breeding process of a dual-purpose line.

New dual-purpose lines were cultivated with the dual-purpose lines cultivated in Examples 1 to 3, and a schematic flow diagram was shown in FIG. 7.

I. Method 1

Crossing combinations were prepared with an excellent line and a blue-grained or dark-blue-grained dual-purpose line of a new system, blue seeds were selected from $F_1$-generation seeds and sown, and according to field performance and indoor seed selection results, an excellent combination in which there was a significant color difference between a blue seed and a white seed or between a blue seed and a red seed was screened out; light-blue/medium-blue seeds were sown, and an $F_2$-generation excellent individual plant in which there was a significant color difference between a blue seed and a white seed or between a blue seed and a red seed was screened out; blue seeds and white or red seeds of each individual plant were separated, and 82 seeds of each color were sown in 2 rows through 5 cm space planting, with a row length of 2 m and a row spacing of 25 cm; a white-grained or red-grained population in which there were about 25% or 100% of sterile plants and a corresponding blue-grained excellent individual plant with prominent agronomic traits were screened out; and the selective breeding was continued until a white-grained or red-grained population in which all individual plants were sterile and had stable and consistent agronomic traits was screened out, which was a new dual-purpose line (excluding dark-blue seeds).

The molecular detection method of the present disclosure (patent application No.: 201810110738.1) can also be used to track and monitor the sterility gene ms1b and purposefully complete the targeted and rapid breeding of next-year multi-generation dual-purpose lines under artificial control conditions. It should be noted that a proportion of white or red seeds of an individual plant or a line screened out in each generation must be greater than or equal to 60%, and corresponding blue-grained individual plants or lines with high outcrossing seeding set of white-grained/red-grained sterile plants are screened out.

II. Method 2

The steps were the same as in method 1 except that crossing combinations were prepared with a sterile line and a blue-grained or dark-blue-grained dual-purpose line of a new system; and only blue seeds were sown for each generation.

III. Sorting and Breeding Methods of Dual-Purpose Lines (Sterile Lines)

The existing wheat color sorters are designed to remove impurities and moldy grains for wheat processing, and color sorter manufacturers include WESORT, Optoplex Corporation, Jiahe Optoelectronic, Meiya Optoelectronic, and the like. Through investigation and experimentation on color sorters of many manufacturers, it is found that the color sorter produced by WESORT is suitable for the sorting of dark-blue, light-blue/medium-blue (dual-purpose line), and white or red seeds. After 2 to 3 times of continuous sorting, a sorting accuracy of blue, white, or red grains can reach 99.9% or higher. The color sorter of WESORT purchased and used is a model of 6SXZ-68. This color sorter was used to complete the sorting of white or red, light/medium-blue (dual-purpose line), and dark-blue seeds, thereby achieving the propagation of dual-purpose lines (sterile lines). The light/medium-blue seeds were used for the propagation of sterile and dual-purpose line seeds.

IV. Screening of Strong-Heterosis Combinations

Figure 8:
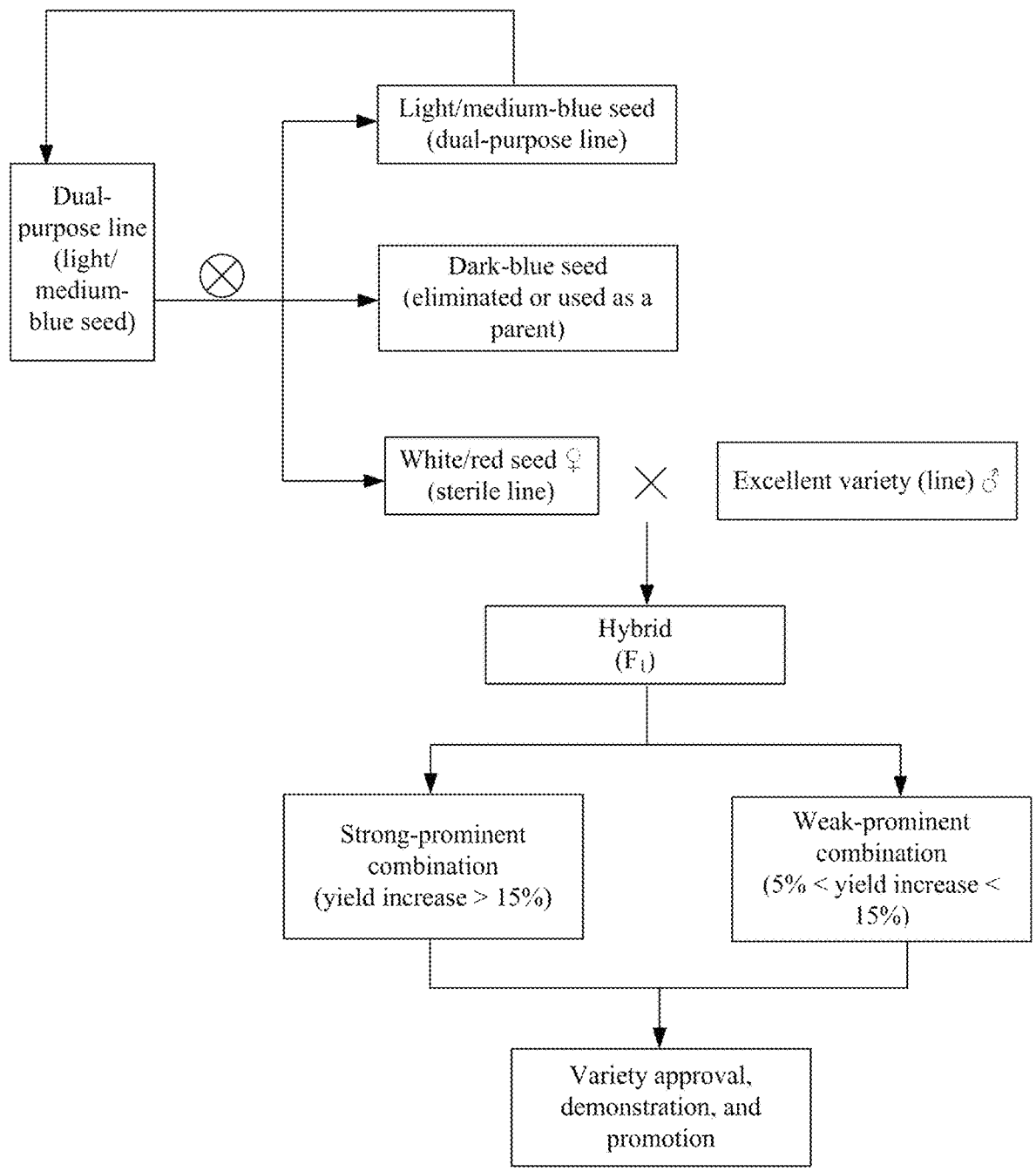
FIG. 8 is a schematic diagram of a breeding process of a strong-heterosis combination (hybrid).

A schematic flow diagram was shown in FIG. 8.

Crossing combinations were prepared with the white-grained sterile lines produced by a number of existing dual-purpose lines and the excellent lines from different ecological regions such as Weilong 121, Weilong 166, 13W8-11, Gaoda No. 1, Shannong 22, Chuanmai 93, 14 Pin 16, 13 Pin 6, Mianmai 827, Mianmai 903, MY6381, Chuanyu 36, Shumai 1671, Chuannong 39, Chuanfumai 14, and Mianmai 906 that could serve as restoring lines, and strong-heterosis combinations were screened out and new hybrid wheat varieties were bred in different ecological regions.

The present disclosure has been described in detail above. Without departing from the purpose and scope of the present disclosure and without unnecessary experimental conditions, the present disclosure can be implemented by those skilled in the art in a wide range under equivalent parameters, concentrations, and conditions. Although specific examples of the present disclosure have been given, it should be understood that the present disclosure can be further modified. In summary, according to the principle of the present disclosure, the present disclosure is intended to encompass any change to, use of, or modification to the present disclosure, including changes made using conventional techniques known in the art, which have departed from the scope disclosed in the present disclosure. Application of some basic features can be done in accordance with the scope of the following accompanying claims.

INDUSTRIAL APPLICATION

The present disclosure discloses a breeding method and use of a blue-grained two-line hybrid wheat system. In the blue-grained two-line hybrid wheat system of the present disclosure, a mixture of white/red seeds (a sterile line) and blue seeds are acquired through selfing of a dual-purpose line, then white/red seeds (the sterile line), light/medium-blue seeds (a dual-purpose line), and dark-blue seeds are separated by a color sorter, the sterile line is used for hybrid production, the light/medium-blue seeds (the dual-purpose lines) are used for propagation of a sterile line and a dual-purpose line, and the dark-blue seeds are eliminated, used as a parent to breed a new sterile line, or used for purification and rejuvenation of a dual-purpose line. The present disclosure has characteristics such as fast sterile line breeding, low hybrid production cost, and strong advantages.

What is claimed is:

1. A breeding method of a blue-grained two-line hybrid wheat system, comprising the following steps:

(1) providing a double-ditelosomic seed carrying a translocated telosome T4AgL fragment (Ba)-4BL. and a telosome 4thS fragment (Rf).;

(2) subjecting the double-ditelosomic seed obtained in step (1) to a mutagenesis treatment, and sowing the double-ditelosomic seed to cultivate a plant;

(3) crossing the plant grown from the double-ditelosomic seed obtained in step (1) as a male parent with a white-grained sterile plant as a female parent, harvesting seeds on the female parent plant, selecting a blue seed, subjecting the blue seed to a mutagenesis treatment, and sowing the blue seed to cultivate a plant, wherein the white-grained sterile plant is a male-sterile plant grown from a white seed obtained from selfing of a dual-purpose line 15L4167, and the dual-purpose line 15L4167 is the addition line carrying the translocated chromosome T4AgL fragment (Ba)-4BL.4thS (Rf);

(4) crossing the plant obtained in step (2) or (3) as a male parent with a white-grained sterile plant as a female parent, harvesting seeds on the female parent plant, and screening out blue seeds, wherein the white-grained sterile plant is a male-sterile plant grown from a white seed obtained from selfing of a dual-purpose line 15L4167;

(5) sowing the blue seeds obtained in step (4) to cultivate plants, eliminating male-sterile plants, selfing a selected plant, harvesting seeds, and sowing selected seeds to cultivate plants each with both blue seeds and white seeds;

(6) sorting white seeds and blue seeds obtained from selfing of each of the plants screened out in step (5); and (7) sowing the white seeds and the blue seeds obtained in step (6) to cultivate plants; and if all plants grown from blue seeds of an individual plant are male-fertile plants and all plants grown from white seeds of the individual plant are male-sterile plants, subjecting blue seeds of the individual plant to microscopic examination to obtain a plant line carrying a translocated telosome T4thS fragment (Rf)-4AgL fragment (Ba)-4BL., which is a dual-purpose line with light-blue/medium-blue seeds.

* * * * *